(12) United States Patent
Callewaert et al.

(10) Patent No.: US 10,941,418 B2
(45) Date of Patent: Mar. 9, 2021

(54) MEANS AND METHODS FOR GENERATING COMPLEX GLYCANS DERIVED FROM FUNGAL ENGINEERED HOSTS

(71) Applicants: VIB VZW, Ghent (BE); UNIVERSITEIT GENT, Ghent (BE)

(72) Inventors: Nico L. M. Callewaert, Nevele (BE); Bram Laukens, Ghent (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 15 days.

(21) Appl. No.: 16/097,951

(22) PCT Filed: May 3, 2017

(86) PCT No.: PCT/EP2017/060568
§ 371 (c)(1),
(2) Date: Oct. 31, 2018

(87) PCT Pub. No.: WO2017/191208
PCT Pub. Date: Nov. 9, 2017

(65) Prior Publication Data
US 2019/0144889 A1 May 16, 2019

(30) Foreign Application Priority Data
May 3, 2016 (EP) .................................... 16168156

(51) Int. Cl.
| | | |
|---|---|---|
| C12N 15/52 | (2006.01) | |
| C12P 1/02 | (2006.01) | |
| C12P 21/00 | (2006.01) | |
| A61K 38/17 | (2006.01) | |

(52) U.S. Cl.
CPC ............ *C12P 1/02* (2013.01); *A61K 38/1741* (2013.01); *C12P 21/00* (2013.01); *C12P 21/005* (2013.01); *C12Y 302/01096* (2013.01)

(58) Field of Classification Search
CPC .................................................. C12P 21/005
See application file for complete search history.

(56) References Cited

U.S. PATENT DOCUMENTS

2017/0159094 A1* 6/2017 Natunen ................ C12P 21/005

FOREIGN PATENT DOCUMENTS

| WO | WO2010015722 A1 | 2/2010 |
|---|---|---|
| WO | WO2015102501 A1 | 7/2015 |

OTHER PUBLICATIONS

Anyaogu et al. "Manipulating the Glycosylation Pathway in Bacterial and Lower Eukaryotes for Production of Therapeutic Proteins", Current Opinion in biotechnology, vol. 36, Sep. 1, 2015, pp. 122-128, XP029346463.

Claes et al. "Modular Integrated Secretory System Engineering in Pichia Pastoris to Enghance Integral Membrane Protein Expression" Pichia 2016 Conference, Apr. 3-6, 2016, Antalya, Turkey book of Abstracts, Apr. 2016, p. 21. XP002770729. Retrieved from the Internet URL: http://www.pichia2016.com/en/images/Pichia2016AbstractBookFinal.pdf.

Dicker et al. "Using Glyco-Engineering to Produce Therapeutic Proteins", Expert Opinion on Biological Therapy, vol. 15, 2015, pp. 1501-1516, XP002762511.

Fidan et al. "Recent Advances in Engineering Yeast for Pharmaceutical Production", RSC Advances, vol. 5, 2015, pp. 86665-86674, XP002762509.

Gerlach et al. "Differential Release of High Mannose Structural Isoforms by Fungal and Bacertial Endo-Beta-N-Acetylglucosaminidases", Molecular Biosystems, vol. 8, 2012, pp. 1472-1481, XP002762538.

Gomathinayagam et al. "In vitro enzymatic treatment to remove 0-linked mannose from intact glycoproteins", Applied Biology and Biotechnology, vol. 98, 2014, pp. 2545-2554, XP035328343.

Hopkins et al. "A Practical Approach for O-Linked Mannose Removal: the Use of Recombinant Lysosomal Mannosidase", Applied Microbiology and Biotechnology, vol. 99, 2015, pp. 3913-3927, XP035482670.

Laukens et al. "N-Glycosylation Galore Personalizing and Cusotmizing N-Glycans Beyond GlycoSwitch", Pichia 2014 Conference, Mar. 2-5, 2014, San Diego, U.S.A, Book of Abstracts, 2014, pp. 55, XP002770731, Rerived from the Internet URL: http://pichia.com/wp-content/uploads/2014/12/Pichia_2014_Conference_Book.pdf.

PCT International Search Report and Written Opinion, Application No. PCT/EP2017/060568, dated Jun. 19, 2017.

Stals et al. "High Resolution Crystal Structure of the Endo-N-Acetyl-Beta-D-Glucosaminidase Responsible for the Deglycosylation of Hypocrea Jecorina Cellulases", PLOS One, vol. 7, 2012, pp. 1-13. XP002762525.

Wang et al. "High-Level Expression of Endo-Beta-N-Acetylglucosaminidase H from *Streptomyces plicatus* in Pichia Pastoris and Its Application for the Deglycosylation of Glycoproteins", PLOS One, vol. 10, 2015 pp. 1-17, XP055287204.

Zimecki et al. "The Effect of Carbohydrate Moiety Structure on the lmmunoregulatory Activity of Lactoferrin in Vitro" Cellular Molecular Biology Letters, vol. 19, 2014, pp. 284-296, XP035994806.

\* cited by examiner

*Primary Examiner* — Tekchand Saidha
(74) *Attorney, Agent, or Firm* — Patent Law Works, LLP

(57) ABSTRACT

The present application relates to the field of glyco-engineering, more specifically to glycosylation-engineered fungal cells, more specifically glycosylation-engineered yeast cells, optimized to produce highly homogenous forms of complex N-glycans on recombinant proteins. The invention specifically relates to methods to obtain pharmaceutical compositions comprising recombinant glycoproteins which have homogenous forms of complex N-glycans. In addition, the invention relates to novel pharmaceutical compositions which result from the methods of the invention.

11 Claims, 22 Drawing Sheets
Specification includes a Sequence Listing.

N-glycan quantification of $Gal_2GlcNAc_2Man_3GlcNAc_2$ $IL22^{N21}$
With Endoglucosaminidase clean-up

|  | AUC total | AUC JB | AUC Unknown | AUC Complex |
|---|---|---|---|---|
| (RFU) | 125736 | 149 | 1969 | 123618 |
|  |  |  | Complex (% of total) | 98,32 |
|  |  |  | Background (% of total) | 1,68 |
|  |  |  | Total | 100 |

Without Endoglucosaminidase clean-up

|  | AUC total | AUC JB | AUC Unknown | AUC Complex |
|---|---|---|---|---|
| (RFU) | 63100 | 9558 | 2873 | 50669 |
|  |  |  | Complex (% of total) | 80,30 |
|  |  |  | Background (% of total) | 19,70 |
|  |  |  | Total | 100 |

N-glycan quantification of $Gal_2GlcNAc_2Man_3GlcNAc_2$ $IL22^{WT}$
With Endoglucosaminidase clean-up

|  | AUC total | AUC JB | AUC Unknown | AUC Complex |
|---|---|---|---|---|
| (RFU) | 57979 | 365 | 3436 | 54178 |
|  |  |  | Complex (% of total) | 93,44 |
|  |  |  | Background (% of total) | 6,56 |
|  |  |  | Total | 100 |

Without Endoglucosaminidase clean-up

|  | AUC total | AUC JB | AUC Unknown | AUC Complex |
|---|---|---|---|---|
| (RFU) | 62323 | 15402 | 8186 | 38735 |
|  |  |  | Complex (% of total) | 62,15 |
|  |  |  | Background (% of total) | 37,85 |
|  |  |  | Total | 100 |

Figure 20

N-glycan quantification of $Gal_2GlcNAc_2Man_3GlcNAc_2$ $IL22^{N21}$

| (RFU) | AUC total | AUC Complex | AUC Gal | AUC Gal2 | AUC Gn2 | AUC background |
|---|---|---|---|---|---|---|
| | 50062 | 49189 | 4395 | 43726 | 1068 | 873 |

| | |
|---|---|
| Complex (% of total) | 98,26 |
| Gal2 (% of total) | 87,34 |
| Gal2 (% of complex) | 88,89 |
| Gal (% of complex) | 8,93 |
| Gn2 (% of complex) | 2,17 |
| Total | 100 |

N-glycan quantification of $Gal_2GlcNAc_2Man_3GlcNAc_2$ $IL22^{WT}$

| (RFU) | AUC total | AUC Complex | AUC Gal | UC Gal2 | AUC Gn2 | AUC background |
|---|---|---|---|---|---|---|
| | 274082 | 252848 | 55789 | 167352 | 29707 | 21234 |

| | |
|---|---|
| Complex (% of total) | 92,25 |
| Gal2 (% of total) | 61,06 |
| Gal2 (% of complex) | 66,19 |
| Gal (% of complex) | 22,06 |
| Gn2 (% of complex) | 11,75 |
| Total | 100 |

MEANS AND METHODS FOR GENERATING COMPLEX GLYCANS DERIVED FROM FUNGAL ENGINEERED HOSTS

FIELD OF THE INVENTION

The present application relates to the field of glyco-engineering, more specifically to glycosylation-engineered fungal cells, more specifically glycosylation-engineered yeast cells, optimized to produce highly homogenous forms of complex N-glycans on recombinant proteins. The invention specifically relates to methods to obtain pharmaceutical compositions comprising recombinant glycoproteins which have homogenous forms of complex N-glycans. In addition, the invention relates to novel pharmaceutical compositions which result from the methods of the invention.

BACKGROUND

CHO cell lines are an expression system of choice for biopharmaceuticals and are used for example to make blockbuster monoclonal antibodies like Rituxan, Humira and Enbrel. However, the cost of manufacturing in CHO cell lines is very high and if one wants to make affordable medicines at a lower cost there is a need to shift to alternative host organisms. Glyco-engineered fungal organisms like for example *Pichia pastoris* are able to produce recombinant glycoproteins with complex N-glycosylation structures, but there is need to further engineer the glycosylation capabilities of fungal organisms. Indeed, there is still a significant background of yeast-like sugars present on recombinant proteins. Although a new full *Pichia pastoris* OCH1 knock-out that modifies its glycoproteins predominantly with $Man_8GlcNAc_2$ N-glycans was described recently (Krainer F W et al (2013) *Sci Rep* 3:3279) there was still a considerable amount of background of yeast-type high mannose glycomodifications present when recombinant glycoproteins are produced in this mutant strain. Similar observations were made in earlier reports on OCH1 knock-out strains (Davidson R C et al (2004) *Glycobiology* 14(5):399). In the latter study, the background was attributed mainly to phosphomannosylation and attributed to the presence in the genome of still unknown mannosyltransferases. In the present application we produced different complex glycoforms of IL-22 in complex glyco-engineered *Pichia pastoris* strains. Despite extensive glyco-engineering, we also observed that there was still a considerable, highly heterogeneous background present in the produced glycoforms. Although a part of the heterogeneity originates from intermediates in the sample that did not get fully processed to complex-type N-glycans, it was found that a considerable N-glycan fraction consisted of a range of other oligomannose- and hypermannosyl-type N-glycans. Although there exists the possibility that a fraction of cells in the strains may revert to wild-type OCH1 due to instability of the knock-in construct but it is more likely that other endogenous glycosyltransferases are responsible. We believe that still uncharacterized glycosyltransferases might have a similar activity as Och1p in *Pichia pastoris* and cause heterogeneity in glycoforms, even in complex glyco-engineered strains.

In addition to this, in the present application we have also characterized a novel type of neoglycan on human IL-22 produced in OCH1 mutated *Pichia* strains, comprising of a $Man_5GlcNAc_2$ N-glycan, with a tetra-saccharide modification that had a highly unexpected structure. This tetra-saccharide (Glcα1-2Manβ1-2Manβ1-3Glucα-) substitution is most likely attached to the innermost α-1,3 arm of the mannosyl core. We also observed similar N-glycans on glyco-engineered murine IL-22 (data not shown). Because the identified structure contained β-1,2-mannose residues, a described immunogenic epitope of *C. albicans*, the presence of such N-glycan would hamper the potential for therapeutic use. This particular N-glycan deviates in its structure from a previously described neoglycoform (Gomathinayagam S. et al. (2011). *Glycobiology*. 21(12): 1606-15) showing that our understanding of the N-glycosylation pathway and the endogenous glycosyltransferases is still limited. Moreover, it is also not understood why certain glycoproteins are prone for further modifications whereas others are not.

Despite the genome sequence of *P. pastoris* being available, it is not known which glycosyltransferases are responsible for generating this particular neoglycoform. Therefore, knock-out of specific additional endogenous glycosyltransferases is not straightforward. Although further engineering could partially resolve the substitution by outcompeting endogenous glycosyltransferases, in later stages of the engineering, it is likely that a number of intermediates would re-appear, including hybrid N-glycans, $Man_5GlcNAc_2$ but also oligomannose background of which the structures are difficult to determine with the current techniques. In addition, it is likely that, also neoglycoforms may form on recombinant glycoproteins, even in highly glyco-engineered strains. The only way to prevent or remedy neoglycoform formation, would be to characterize all the potential glycosyltransferases/glycosidases and knock-out these enzymes if they might show some undesired activity. The latter would be an unpractical approach and even then the effect on neoglycoform formation would be unpredictable. Because of the background, the re-appearing intermediates and the possibility of neoglycoform-formation, there exists a clear need to design strategies which allow to remove the remaining fungal-type glycosylation background from the complex N-glycans present on glycoproteins produced in glyco-engineered fungal organisms.

SUMMARY OF THE INVENTION

So far the use of a complex glyco-engineered fungal cell system has mostly focused on exhaustive engineering processes and not on enzymatic treatment (e.g. with specific glycosidase enzymes) after the glycoprotein is produced to remove background since the aim is to keep the N-glycans and not to deglycosylate the glycoprotein. To remove the background of glycoproteins produced in complex N-glycan engineered strains of *Pichia pastoris* it was tested to integrate in vitro enzymatic deglycosylation using the *T. reesei* Endo-β-N-Acetylglucosaminidase EndoT. Recombinant EndoT has been shown to be able to release human Golgi-type oligo-mannose N-glycans but human complex N-glycans are not a substrate for this enzyme (see Stals I. et al (2012) PLOS One 7(7) e40854). However, it was unknown whether the many different types of yeast N-glycans, including some glycoforms triggered by mutation of OCH1, would be eligible substrates and form neoglycoforms. Surprisingly, EndoT performed very well in this task as more than 90% of the background consisting of hybrid N-glycans, yeast high mannose N-glycans and unexpected neoglycoforms disappeared after treatment while the bioactivity of the glycoprotein could be retained.

Moreover, it was found that the in vitro reaction was compatible with the high salt concentrations present in the ammonium sulfate fractions during purification and surprisingly this reaction could be done at 4° C. Since we observed that EndoT was able to work in these unfavorable conditions, it expands its applicability.

The use of complex N-glycosylation glyco-engineered *Pichia*-strains, producing a dominant human complex-type N-glycoform on glycoproteins in combination with an in vitro endoglucosaminidase clean-up step to remove undesired background, provides a powerful tool to make highly pure, customized N-glycoforms of the complex type N-glycans.

Thus where a recombinant glycoprotein, produced in a complex N-glycosylation engineered fungal organism, has one functional N-glycosylation acceptor site then a plurality of glycoforms is produced when this recombinant glycoprotein is purified from the medium and exogenously contacted with a suitable amount of endoglucosaminidase. These glycoforms occur because in the complex N-glycosylation engineered fungal organism a variety of N-glycans are formed: i) hybrid N-glycans, ii) high mannose type N-glycans, iii) unpredictable N-glycan neoglycoforms (see further in the examples section) and iv) the intended complex N-glycans as expected for the specific complex N-glycosylation engineered fungal organism. Contacting with the endoglucosaminidase (e.g. exogenously applied and added in the medium, or added during the purification conditions or added after the purification of the recombinant glycoprotein) will eliminate more than 90% of the hybrid N-glycans and high mannose type N-glycans and also eliminate unpredictable N-neoglycoforms and this will result in the formation of an N-glycan consisting of a single GlcNAc glycan structure. Off note, glycoforms having a single GlcNAc glycan will not be visualized (or cannot be determined) by the method outlined in Examples 2 and 3 but can only be detected by mass spectrometric analysis methods. The resulting complex N-glycans will not be digested upon contacting with the endoglucosaminidase. As a result, a "plurality of glycoforms" of the recombinant glycoprotein will be obtained (estimated by the visualization of the total of all N-glycans present on a recombinant glycoprotein produced in the complex N-glycosylation engineered fungal organism). Hence, plurality refers to N-glycans of the complex type, N-glycans consisting of a single GlcNAc and less than 20%, preferably less than 15%, less than 10%, less than 5% or even less than 1% N-glycans of the hybrid type N-glycans or the high mannose type N-glycans or the N-glycan neoglycoforms.

WO2010/015722 describes the co-expression of an endoglucosaminidase, mammalian glycosyltransferases and a heterologous glycoprotein. In the latter engineered cellular system the endoglucosidase enzyme is targeted to a specific compartment in the Golgi. When the latter system is applied in fungi comprising an exogenous glycoprotein then recombinant glycoproteins comprising N-glycans consisting of a single GlcNAc are produced. The latter is in contrast to the methodology of the invention which is applied in vitro and wherein the complex glyco-engineered fungal cell does not co-express an endoglucosaminidase and where recombinant glycoproteins are produced having a mixture of complex N-glycans and N-glycans consisting of a single GlcNAc. To clarify this even further when a glycoprotein, having only one N-glycosylation acceptor site, is produced in a complex glyco-engineered fungal organism and after the production the resulting glycoprotein is subsequently in vitro treated (or contacted) with an endoglucosaminidase then the glycoforms present on the resulting glycoprotein consist of a mixture of complex N-glycans and N-glycans consisting of a single GlcNAc. When a glycoprotein, having two N-glycosylation acceptor sites, is produced in a complex glyco-engineered fungal organism and after the production the resulting glycoprotein is subsequently in vitro treated (or contacted) with an endoglucosaminidase then the N-glycosylation sites present on a single glycoprotein can consist of either i) one complex N-glycan and the other one single GlcNAc, or ii) both can be a single GlcNAc or iii) both can be a complex N-glycan.

Endoglucosaminidases like EndoH are commonly used to deglycosylate glycoproteins as part of the analytics on SDS-PAGE gel similar to PNGaseF digestion. However, the latter digests are carried out on denatured proteins to determine N-glycosylation profiles on SDS-PAGE with the intent of deglycosylating the protein. Similarly, for crystallography purposes glycoproteins are also often deglycosylated. However, the digests either have to be performed without denaturation or a renaturation/refolding step has to be performed in order to determine the protein structure. The use of endoglucosaminidases as an in vitro clean-up tool (post-fermentation, e.g. during the purification or after the purification) with the aim to further use the obtained glycoprotein for pharmaceutical use has not been investigated in the art. An endoglucosidase clean-up on a complex glyco-engineered yeast platform producing glycoproteins with complex N-glycans has not been reported so far and an in vitro incubation step with an endoglucosaminidase is even considered counterintuitive.

BRIEF DESCRIPTION OF THE FIGURES

FIG. 19. N-glycan quantification. N-glycan quantification and effect of an endoglucosaminidase clean up step performed after the production of the IL-22 glycoprotein. The data show a dramatic increase of complex N-glycan structures after the clean-up procedure FIG. 20. Quantification of galactosylated glycoforms of recombinantly produced IL-22. Specific complex N-glycan quantifications were calculated after the endoglucosaminidase clean-up step.

DETAILED DESCRIPTION

Figure 1:
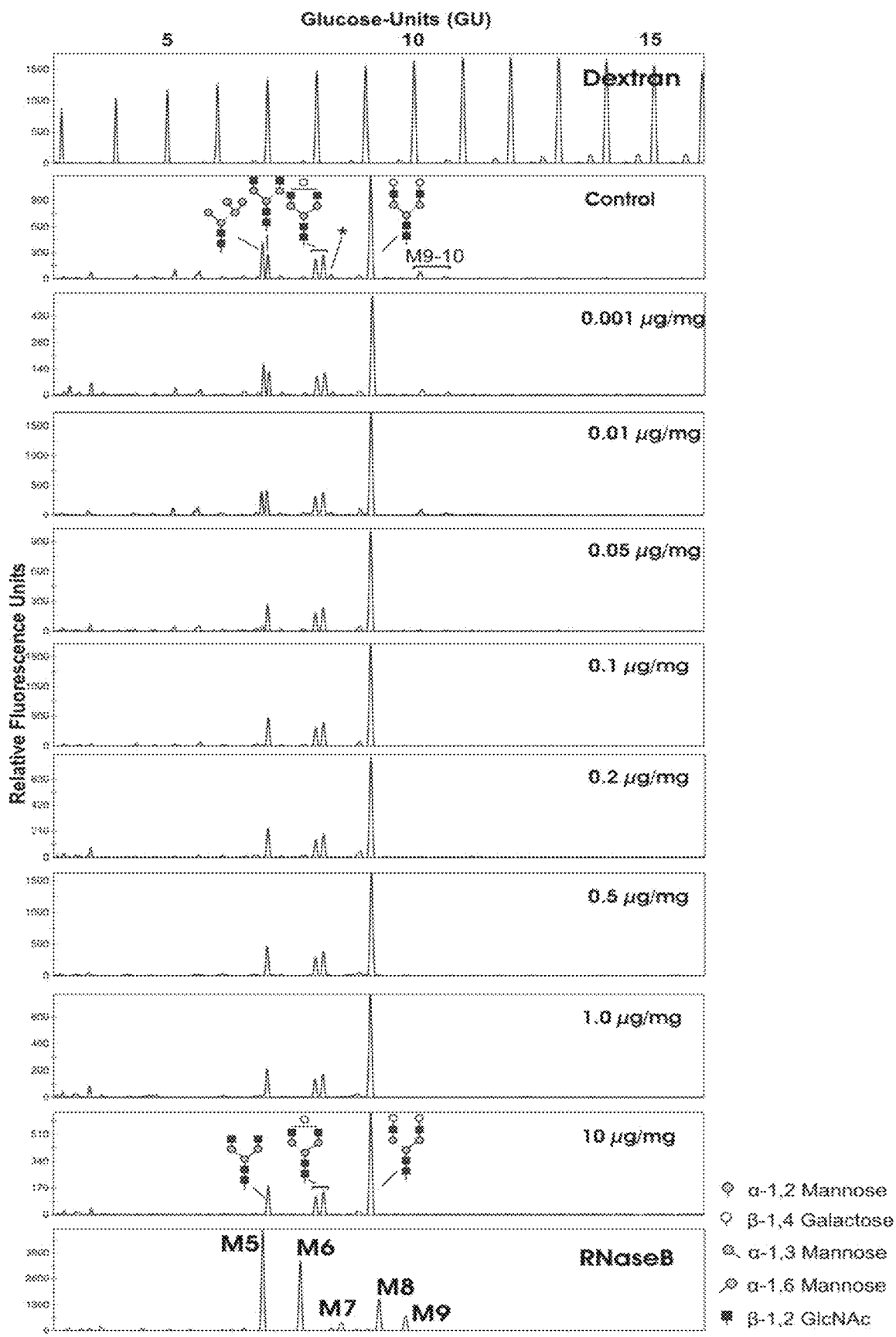
FIG. 1. EndoT dose dose-finding on solubilized $Gal_2Gn_2M_3IL-22^{WT}$ ammonium sulfate fraction at 4° C. The ammonium sulfate precipitated fraction was solubilized and equal amounts of total protein (μg/mg total protein) were digested overnight at 4° C. with increasing amounts of recombinant EndoT. Controls were supplemented with an equal volume 25 mM MES pH5.5 but no EndoT. Proposed N-glycan structures are shown. The top panel (dextran) and bottom panel are a dextran reference standard and the $Man_5GlcNAc_2$ (M5-9) reference N-glycans from RNAseB. Symbols in the legend do not take in account the monosaccharides of the core $Man_1GlcNAc_2$ N-glycan. * represents an unidentified N-glycan.

As used herein, each of the following terms has the meaning associated with it in this section. The articles "a" and "an" are used herein to refer to one or to more than one (i.e., to at least one) of the grammatical object of the article. By way of example, "an element" means one element or more than one element. "About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods. The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments, of the invention described herein are capable of operation in other sequences than described or illustrated herein. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, N.Y. (2012); and Ausubel et al., current Protocols in Molecular Biology (Supplement 100), John Wiley & Sons, New York (2012), for definitions and terms of the art. The definitions provided herein should not be construed to have a scope less than understood by a person of ordinary skill in the art.

As used herein, the term "nucleotide sequence" refers to a polymeric form of nucleotides of any length, either deoxyribonucleotides or ribonucleotides, or analogs thereof. Nucleotide sequences may have any three-dimensional structure, and may perform any function, known or unknown. Non-limiting examples of nucleotide sequences include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleotide sequence may be linear or circular.

As used herein, the term "polypeptide" refers to a polymeric form of amino acids of any length, which can include coded and non-coded amino acids, chemically or biochemically modified or derivatized amino acids, and polypeptides having modified peptide backbones. Polypeptide sequences can be depicted with the single-letter (or one letter) amino acid code or the three letter amino acid code as depicted here below:

| Amino acid | Three letter code | One letter code |
|---|---|---|
| alanine | ala | A |
| arginine | arg | R |
| asparagine | asn | N |
| aspartic acid | asp | D |
| asparagine or aspartic acid | asx | B |
| cysteine | cys | C |
| glutamic acid | glu | E |
| glutamine | gln | Q |
| glutamine or glutamic acid | glx | Z |

-continued

| Amino acid | Three letter code | One letter code |
|---|---|---|
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

The term "expression vector", as used herein, includes any vector known to the skilled person, including plasmid vectors, cosmid vectors, phage vectors, such as lambda phage, viral vectors, such as adenoviral, AAV or baculoviral vectors, or artificial chromosome vectors such as bacterial artificial chromosomes (BAC), yeast artificial chromosomes (YAC), or P1 artificial chromosomes (PAC). Expression vectors generally contain a desired coding sequence and appropriate promoter sequences necessary for the expression of the operably linked coding sequence in a particular host organism (e.g. higher eukaryotes, lower eukaryotes, prokaryotes).

Typically, a vector comprises a nucleotide sequence in which an expressible promoter or regulatory nucleotide sequence is operatively linked to, or associated with, a nucleotide sequence or DNA region that codes for an mRNA, such that the regulatory nucleotide sequence is able to regulate transcription or expression of the associated nucleotide sequence. Typically, a regulatory nucleotide sequence or promoter of the vector is not operatively linked to the associated nucleotide sequence as found in nature, hence is heterologous to the coding sequence of the DNA region operably linked to. The term "operatively" or "operably" "linked" as used herein refers to a functional linkage between the expressible promoter sequence and the DNA region or gene of interest, such that the promoter sequence is able to initiate transcription of the gene of interest, and refers to a functional linkage between the gene of interest and the transcription terminating sequence to assure adequate termination of transcription in eukaryotic cells. An "inducible promoter" refers to a promoter that can be switched 'on' or 'off' (thereby regulating gene transcription) in response to external stimuli such as, but not limited to, temperature, pH, certain nutrients, specific cellular signals, et cetera. It is used to distinguish between a "constitutive promoter", by which a promoter is meant that is continuously switched 'on', i.e. from which gene transcription is constitutively active.

A "glycan" as used herein generally refers to glycosidically linked monosaccharides, oligosaccharides and polysaccharides. Hence, carbohydrate portions of a glycoconjugate, such as a glycoprotein, glycolipid, or a proteoglycan are referred to herein as a "glycan". Glycans can be homo- or heteropolymers of monosaccharide residues, and can be linear or branched. N-linked glycans may be composed of GalNAc, Galactose, neuraminic acid, N-acetylglucosamine, Fucose, Mannose, and other monosaccharides, as also exemplified further herein.

In eukaryotes, O-linked glycans are assembled one sugar at a time on a serine or threonine residue of a peptide chain in the Golgi apparatus. Unlike N-linked glycans, there are no known consensus sequences but the position of a proline residue at either −1 or +3 relative to the serine or threonine is favourable for O-linked glycosylation.

A "glyco-engineered cell" refers to a cell that has been genetically modified so that it expresses proteins with an altered N-glycan structure and/or O-glycan structure as compared to in a wild type background. Typically, the naturally occurring modifications on glycoproteins have been altered by genetic engineering of enzymes involved in the glycosylation pathway. In general, sugar chains in N-linked glycosylation may be divided in three types: high-mannose (typically yeast), complex (typically mammalian) and hybrid type glycosylation. Besides that, a variety of O-glycan patterns exist, for example with yeast oligomannosylglycans differing from mucin-type O-glycosylation in mammalian cells. The different types of N- and O-glycosylation are all well known to the skilled person and defined in the literature. Considerable effort has been directed towards the identification and optimization of strategies for the engineering of eukaryotic cells that produce glycoproteins having a desired N- and/or O-glycosylation pattern and are known in the art (e.g. De Pourcq, K. et al., Appl Microbiol Biotechnol. 87(5), 2010). One non-limiting example of such a glyco-engineered expression system is described in patent application WO2010015722 and relates to a (higher or lower) eukaryotic cell expressing both an endoglucosaminidase and a target protein, and wherein the recombinant secreted target proteins are characterized by a uniform N-glycosylation pattern (in particular one single GlcNAc residue (in lower eukaryotes) or a modification thereof such as GlcNAc modified with Galactose (LacNAc) or sialyl-LacNAc (in mammalian cells). Also encompassed are cells genetically modified so that they express proteins or glycoproteins in which the glycosylation pattern is human-like or humanized (i.e. complex-type glycoproteins). This can be achieved by providing cells, in particular lower eukaryotic cells, having inactivated endogenous glycosylation enzymes and/or comprising at least one other exogenous nucleic acid sequence encoding at least one enzyme needed for complex glycosylation. Endogenous glycosylation enzymes which could be inactivated include the alpha-1,6-mannosyltransferase Och1p, Alg3p, alpha-1,3-mannosyltransferase of the Mnn1p family, beta-1,2-mannosyltransferases. Enzymes needed for complex glycosylation include, but are not limited to: N-acetylglucosaminyl transferase I, N-acetylglucosaminyl transferase II, mannosidase II, galactosyltransferase, fucosyltransferase and sialyltransferase, and enzymes that are involved in donor sugar nucleotide synthesis or transport. Still other glyco-engineered cells, in particular yeast cells, that are envisaged here are characterized in that at least one enzyme involved in the production of high mannose structures (high mannose-type glycans) is not expressed. Enzymes involved in the production of high mannose structures typically are mannosyltransferases. In particular, alpha-1,6-mannosyltransferases Och1p, Alg3p, alpha-1,3-mannosyltransferase of the Mnn1p family, beta-1,2-mannosyltransferases may not be expressed. Thus, a cell can additionally or alternatively be engineered to express one or more enzymes or enzyme activities, which enable the production of particular N-glycan structures at a high yield. Such an enzyme can be targeted to a host subcellular organelle in which the enzyme will have optimal activity, for example, by means of signal peptide not normally associated with the enzyme. It should be clear that the enzymes described herein and their activities are well-known in the art.

'Glycoproteins' as used in the application refers to proteins that, in their normal physiological context and/or their functional form, contain oligosaccharide chains (glycans) covalently attached to their polypeptide side-chains. In addition, a glycoprotein is any protein with an artificially introduced glycosylation site. Typically a glycoprotein, typically a recombinant glycoprotein, for example a heterologous recombinant glycoprotein (which does not occur normally in the fungal or yeast organism) is produced as several glycoforms when it is made in a glycosylation-engineered fungal or yeast organism. Different glycoforms (even originating from one specific functional N-glycosylation site on a (recombinant) glycoprotein) occur because of the very nature of the process of N-glycosylation. By nature the formation of complex N-glycosylation glycans (especially in a complex N-glycosylation engineered fungal organism) is never 100% efficient and hence different glycoforms occur on a specific N-glycan position present on a glycoprotein. Thus it is possible that in a glycoprotein (e.g. a glycoprotein with 2 N-glycan acceptor sites) one N-glycan is a complex N-glycan and the other N-glycan is a hybrid glycan or a high-mannose type glycan. In particular, glycoproteins as used herein are proteins that show N-glycosylation in their physiologically active form. Thus, glycoproteins typically contain a sugar chain at least on one asparagine residue. A non-limiting list of glycoproteins is provided in the specification. The term 'glycoproteins' is not intended to refer to the length of the amino acid chain, 'glycopeptides' are included within the definition of 'glycoproteins'.

The terms '(glyco)protein' and 'enzyme' (e.g. endoglucosaminidase, glycosyltransferase, mannosidase, mannosyltransferase) as used in the application are also intended to cover functionally active fragments and variants of the naturally occurring proteins. Indeed, for many (e.g. therapeutic) proteins, part of the protein may be sufficient to achieve an (e.g. therapeutic, enzymatic) effect. The same applies for variants (i.e. proteins in which one or more amino acids have been substituted with other amino acids, but which retain functionality or even show improved functionality), in particular for variants of the enzymes optimized for enzymatic activity. In the context of the application, a glycoprotein refers to the protein itself; a glycoprotein may be either in its glycosylated or non-glycosylated form. A 'glycosylated' protein is a (glyco)protein that carries at least one oligosaccharide chain. An N-glycosylated protein, particularly an N-glycosylated recombinant glycoprotein, is a glycoprotein which carries at least one oligosaccharide chain on an N-glycan.

A 'glycoform' as used in the present invention is a variant of a glycosylated glycoprotein wherein the variation is in the N-glycan composition present on said glycoprotein.

A 'sugar chain', 'oligosaccharide chain' or 'carbohydrate chain' as used herein is referred in the claims as an N-glycan (with N- referring to N-glycosylation). Sugar chains may be branched or not, and may comprise one or more types of oligosaccharide. In general, sugar chains in N-linked glycosylation may be divided in three types: high-mannose, complex and hybrid type glycosylation. These terms are well known to the skilled person and defined in the literature. Briefly, high-mannose type glycosylation typically refers to oligosaccharide chains comprising two N-acetylglucosamines with (possibly many) mannose and/or mannosylphosphate residues (but typically no other monosaccharides).

Complex glycosylation typically refers to structures with typically one, two or more (e.g. up to six) outer branches, most often linked to an inner core structure $Man_3GlcNAc_2$.

For instance, a complex N-glycan may have at least one branch, or at least two, of alternating GlcNAc and optionally also galactose (Gal) residues that may terminate in a variety of oligosaccharides but typically will not terminate with a mannose residue. Several examples of complex N-glycans made in complex N-glycosylation engineered fungal organisms are shown in the appended example section. For the sake of clarity a single GlcNAc present on an N-glycosylation site of a glycoprotein is not regarded as a complex N-glycan.

Hybrid type glycosylation covers the intermediate forms, i.e. those glycosylated proteins carrying both terminal mannose and terminal non-mannose residues in addition to the two N-acetylglucosamine residues. In contrast to complex glycosylation, at least one branch of hybrid type glycosylation structures ends in a mannose residue. Hybrid N-glycans can originate from the inefficient glycosylation of the heterologous glycosyltransferase enzyme present in a complex N-glycosylation engineered fungal organism.

'Complex N-glycosylation-engineered fungal organism' as used in the application are fungal cells that express at least one exogenous nucleic acid sequence encoding an enzyme needed for complex N-glycosylation that is not expressed in the wild-type fungal organism, and/or that do not express at least one enzyme involved in the production of high-mannose type structures that is normally expressed in the wild type fungus. Particularly, complex N-glycosylation-engineered fungal organisms are complex N-glycosylation-engineered yeasts. Non-limiting examples of yeasts which can be engineered towards complex N-glycosylation-engineered yeasts comprise *Saccharomyces* species (e.g. *Saccharomyces cerevisiae*), a *Hansenula* species (e.g. *Hansenula polymorpha*), an *Arxula* species (e.g. *Arxula adeninivorans*), a *Yarrowia* species (e.g. *Yarrowia lipolytica*), a *Kluyveromyces* species (e.g. *Kluyveromyces lactis*), or *Komagataella phaffii* (Kurtzman, C. P. (2009) J Ind Microbiol Biotechnol. 36(11) which was previously named and better known under the old nomenclature as *Pichia pastoris* and also further used herein. According to a specific embodiment, the lower eukaryotic cells are *Pichia* cells, and in a most particular embodiment *Pichia pastoris* cells. Still other 'complex N-glycosylation-engineered fungal organisms comprise *Myceliopthora thermophila* (also known as C1 by the company Dyadic), *Aspergillus* species (e.g. *Aspergillus nidulans, Aspergillus niger, Aspergillus oryzae, Aspergillus japonicus*), *Fusarium* species (e.g. *Fusarium venenatum*), *Hypocrea* and *Trichoderma* species (e.g. *Trichoderma reesei*).

According to particular embodiments, the enzyme needed for complex N-glycosylation is a mannosidase or a glycosyltransferase other than a mannosyltransferase. According to further particular embodiments, the at least one enzyme needed for complex glycosylation is selected from the group consisting of N-acetylglucosaminyl transferase I, N-acetylglucosaminyl transferase II, mannosidase II, galactosyltransferase, and sialyltransferase.

According to particular embodiments, the complex N-glycosylation yeast cell (or in short glycosylation-engineered yeast cell or glyco-engineered yeast cell) may be characterized in that at least one enzyme involved in the production of high mannose structures (high mannose-type glycans) is not expressed (or is not as functionally active in the cell as in a wild-type cell). According to further particular embodiments, at least one mannosyltransferase is not expressed in the glyco-engineered yeast cell. Typically, the mannosyltransferase that is not expressed in the glyco-engineered yeast cell is expressed in the wild-type counterpart of the yeast cell. According to yet further particular embodiments, the mannosyltransferase is a α-1,2-mannosyltransferase, α-1,3-mannosyltransferase, α-1,6-mannosyltransferase, or β-1,4-mannosyltransferase. These proteins often have specific names in yeast (e.g. Alg, Och, Mnn), but their activities are well known in the art. Alternatively or additionally, at least one mannosylphosphate transferase is not functionally active in the complex N-glycosylation-engineered yeast cell.

An 'endoglucosaminidase' as used herein refers to enzymes that hydrolyse the bond between the anomeric carbon of a non-terminal beta-linked N-acetylglucosamine residue in an oligosaccharide of a glycoprotein or a glycolipid, and its aglycon, thereby releasing mono- or oligosaccharides from glycoproteins or glycolipids or sugar polymers. Endoglucosaminidases are a subset of the glycosidases, and may or may not have other enzymatic activities (such as e.g. glycosyltransferase activity). A particular class of endoglucosaminidases is formed by the endo-β-N-acetylglucosaminidases or mannosyl-glycoprotein endo-β-N-acetylglucosaminidases, indicated as EC 3.2.1.96 in the International Union of Biochemistry and Molecular Biology (IUBMB) nomenclature. This particular class of enzymes are capable of catalyzing the endohydrolysis of the N,N'-diacetylchitobiosyl unit in high-mannose glycopeptides and glycoproteins containing the -[Man (GlcNAc)$_2$]Asn- structure. One N-acetyl-D-glucosamine (GlcNAc) residue remains attached to the protein; the rest of the oligosaccharide is released intact. The result thus is a single GlcNAc-modified N-glycosylation site present on a glycoprotein. Glycoproteins with a modified GlcNAc residue will still be referred to as single GlcNAc-modified proteins, as there is no second sugar residue on position 4 of the GlcNAc residue (i.e. there is no typical sugar chain). A non-limiting list of endoglucosaminidases is provided further in the application.

Particularly with regard to the N-glycosylation-engineered fungal or yeast cells, an 'enzyme needed for complex glycosylation' as used herein refers to any enzyme not naturally occurring in the host fungal or yeast cell that may be involved in the synthesis of complex glycans as found in higher eukaryotes, in particular as found in mammals, more in particular as found in humans. Most particularly, such enzymes are enzymes that remove mannose residues from the sugar chain (i.e. mannosidases) or glycosyltransferases, in particular glycosyltransferases other than mannosyltransferases (i.e. glycosyltransferases that transfer monosaccharides that are not found in high-mannose glycans) and/or phosphomannosyltransferases.

A 'glycosyltransferase' as used in the application is any of a group of enzymes that catalyze the transfer of glycosyl groups in biochemical reactions, in particular glycosyl transfer to asparagine-linked sugar residues to give N-linked glycoproteins. Glycosyltransferases fall under EC 2.4 in the IUBMB nomenclature, a particular class of glycosyltransferases are hexosyltransferases (EC 2.4.1). Among the wide variety of these post-translational enzymes that process peptides into glycoproteins are enzymes such as, but not limited to, N-acetylglucosaminyl transferases, N-acetylgalactosaminyltransferases, sialyltransferases, fucosyltransferases, galactosyltransferases, and mannosyltransferases.

Note that exogenous mannosyltransferases are excluded for specific embodiments of N-glycosylation-engineered yeast cells described in the application. 'Mannosyltransferases' as used in the application refers to enzymes that catalyze the transfer of a mannosyl group to an acceptor molecule, typically another carbohydrate, in the Golgi apparatus. Mannosyltransferases are typically endogenous enzymes in fungi and yeast and involved in the synthesis of high-mannose type glycans.

Of note, an enzyme may possess glycosyltransferase activity next to its endoglucosaminidase activity. Although it may be possible to use one enzyme to exert these two activities, typically the enzymes used will fulfill only one function. Thus, it is envisaged to use enzymes that have been modified or mutated to make sure they perform only one function, or that have been modified or mutated to ensure they carry out a specific function more efficiently. Such modified enzymes are known in the art.

The present invention aims to provide compositions, particularly pharmaceutical compositions, comprising homogenous forms of N-glycans, particularly complex N-glycans present on a recombinant glycoprotein. Such recombinant glycoproteins are produced in complex N-glycosylation-engineered fungal organisms.

In one embodiment the invention provides a composition comprising a plurality of a recombinant glycoprotein, wherein the N-glycans present on said glycoforms comprise a mixture of complex N-glycans and an N-glycan structure consisting of a single GlcNAc and wherein said combined complex N-glycans and N-glycans consisting of a single GlcNAc are present at a level of higher than 90% of the total N-glycans in said composition.

In yet another embodiment the invention provides a composition comprising a plurality of glycoforms of a recombinant glycoprotein, wherein the N-glycans present on said glycoforms comprise a mixture of complex N-glycans and an N-glycan structure consisting of a single GlcNAc and wherein said complex N-glycans are present at a level of higher than 90% of the total N-glycans in said composition.

In yet another embodiment the invention provides a purified composition comprising a plurality of a recombinant glycoprotein, wherein the N-glycans present on said glycoforms comprise a mixture of complex N-glycans and an N-glycan structure consisting of a single GlcNAc and wherein said combined complex N-glycans and N-glycans consisting of a single GlcNAc are present at a level of higher than 90% of the total N-glycans in said composition.

In yet another embodiment the invention provides a purified composition comprising a plurality of glycoforms of a recombinant glycoprotein, wherein the N-glycans present on said glycoforms comprise a mixture of complex N-glycans and an N-glycan structure consisting of a single GlcNAc and wherein said complex N-glycans are present at a level of higher than 90% of the total N-glycans in said composition.

This is achieved, according to a specific aspect, by providing complex N-glycosylation-engineered fungal organisms with an exogenous nucleic acid sequence encoding a glycoprotein and contacting the secreted glycoprotein in vitro (e.g. by addition to the fermentation medium or by addition to the purified glycoprotein or by addition during the purification of the glycoprotein) with a suitable amount of an endoglucosaminidase. Typically, said endoglucosaminidase is recombinantly produced in a suitable host cell, upscaled and purified and added to the secreted glycoprotein present in the growth medium of the complex N-glycosylation engineered fungal organism. Importantly, said endoglucosaminidase is not produced by the same cell that also expresses the glycoprotein of interest. In a specific embodiment said endoglucosaminidase is applied to the recombinant glycoprotein during the purification of the recombinant glycoprotein. In yet another specific embodiment said endoglucosaminidase is applied to the recombinant glycoprotein after the purification of the recombinant glycoprotein.

In yet another embodiment the invention provides a composition comprising a plurality of glycoforms of a recombinant glycoprotein, wherein the N-glycans present on said glycoforms comprise a mixture of complex N-glycans and an N-glycan structure consisting of a single GlcNAc wherein said combined complex N-glycans and N-glycans consisting of a single GlcNAc are present at a level of higher than 90% of the total N-glycans in said composition wherein said composition is obtained by production of said glycoprotein in a complex N-glycosylation-engineered fungal organism comprising cultivating said recombinant complex N-glycosylation engineered fungal organism comprising an exogenous genetic construct encoding said glycoprotein under conditions wherein said glycoprotein is expressed and contacting said recombinant glycoprotein with the addition of an endoglucosaminidase.

In yet another embodiment the invention provides a composition comprising a plurality of glycoforms of a recombinant glycoprotein, wherein the N-glycans present on said glycoforms comprise a mixture of complex N-glycans and an N-glycan structure consisting of a single GlcNAc wherein said complex N-glycans are present at a level of higher than 90% of the total N-glycans in said composition wherein said composition is obtained by production of said glycoprotein in a complex N-glycosylation-engineered fungal organism comprising cultivating said recombinant complex N-glycosylation engineered fungal organism comprising an exogenous genetic construct encoding said glycoprotein under conditions wherein said glycoprotein is expressed and contacting said recombinant glycoprotein with the addition of an endoglucosaminidase.

The nature of the glycoprotein is not critical to the invention, but glycoproteins will typically be proteins relevant for medicine and/or industry for which homogenous N-glycosylation is important. Non-limiting examples include many hormones, growth factors, cytokines and their corresponding receptors, such as follicle-stimulating hormone (FSH), luteinizing hormone (LH), thyroid-stimulating hormone (TSH), epidermal growth factor (EGF), human epidermal growth factor receptor-2 (HER-2), fibroblast growth factor-alpha (FGF-α), fibroblast growth factor-beta (FGF-β), transforming growth factor-alpha (TGF-α), transforming growth factor-beta (TGF-β), platelet-derived growth factor (PDGF), insulin-like growth factor-1 (IGF-1), insulin-like growth factor-2 (IGF-2), nerve growth factor (NGF), nerve growth factor-beta (NGF-β); receptors of the aforementioned, growth hormones (e.g., human growth hormone, bovine growth hormone); insulin (e.g., insulin A chain and insulin B chain), proinsulin; erythropoietin (EPO); colony stimulating factors (e.g., granulocyte colony-stimulating factor (G-CSF), granulocyte macrophage colony-stimulating factor (GM-CSF), macrophage colony-stimulating factor (M-CSF)); interleukins (e.g., IL-1 through IL-33); vascular endothelial growth factor (VEGF) and its receptor (VEGF-R); interferons (e.g., IFN-α, β, or γ); tumor necrosis factor (e.g., TNF-α and TNF-β) and their receptors, TNFR-1 and TNFR-2; thrombopoietin (TPO); thrombin; brain natriuretic peptide (BNP); clotting factors (e.g., Factor VIII, Factor IX, von Willebrands factor, and the like); anti-clotting factors; tissue plasminogen activator (TPA), e.g., urokinase or human urine or tissue type TPA; calcitonin; CD proteins (e.g., CD3, CD4, CD8, CD28, CD19, etc.); CTLA proteins (e.g., CTLA4); T-cell and B-cell receptor proteins; antibodies, bone morphogenic proteins (BMPs, e.g., BMP-1, BMP- 2, BMP-3, etc.); neurotrophic factors, e.g., bone derived neurotrophic factor (BDNF); neurotrophins, e.g., NT3-6; renin; rheumatoid factor; RANTES; albumin; relaxin; macrophage inhibitory protein (e.g., MIP-1, MIP-2); viral proteins or antigens; surface membrane proteins; ion channel proteins; enzymes; alkaline phosphatase; lectins; regulatory proteins; antibodies; immunomodulatory proteins, (e.g., HLA, MHC, the B7 family); homing receptors; transport proteins; superoxide dismutase (SOD); G-protein coupled receptor proteins (GPCRs); neuromodulatory proteins; Alzheimer's Disease associated proteins and peptides, (e.g., A-beta), and others as known in the art, including fusion or chimeric proteins of the above.

The nature of the endoglucosaminidase will depend on the desired glycopopulation of the glycoproteins. For instance, endoglucosaminidases may be selected for their substrate specificity. Some endoglucosaminidases, e.g. Endo H and Endo T, hydrolyse high-mannose type sugar chains and hybrid type sugars, but leave complex carbohydrate structures intact.

Such enzymes are ideal e.g. for obtaining N-glycans consisting of complex N-glycans and for removing undesired high-mannose and/or hybrid type sugars from produced glycoproteins and as we have unexpectedly observed shown in the examples of the present invention also for the removal of N-glycan neoglycoforms on recombinant glycoproteins expressed in a complex N-glycosylation engineered fungal organism. According to particular embodiments, the endoglucosaminidase hydrolyses high mannose-type sugar chains, hybrid-type glycans, N-glycan neoglycoforms but not complex-type glycans.

Endoglucosaminidases may also have substrate specificity with regard to the glycoprotein (instead of only the sugar chain), some endoglucosaminidases are e.g. more successful in hydrolyzing sugar chains from (particularly compactly folded) proteins than other endoglucosaminidases (e.g. Endo T), others may (also) be particularly successful in hydrolyzing sugar chains from glycopeptides or not-compactly folded proteins (e.g. Endo H, Endo T). Importantly, as this typically has to do with access to or availability of the substrate rather than with the specificity of the endoglucosaminidase, this does not exclude the use of certain enzymes for specific proteins, but some endoglucosaminidases may require more time to complete the hydrolysis of all N-linked sugar structures. The hydrolysis of high-mannose N-glycans or hybrid N-glycans by Endo T or Endo H present on N-glycosylated proteins produced in complex glyco-engineered fungal cells (like *Pichia pastoris*) leads to N-glycans consisting of a single GlcNAc. A particular preferred class of endoglucosaminidases is formed by the mannosyl-glycoprotein endo-β-N-acetylglucosaminidases, indicated as EC 3.2.1.96 in the IUBMB nomenclature. These enzymes can remove sugar chains (hybrid N-glycans, high mannose N-glycans and neoglycoforms of N-glycans as shown herein) while leaving one GlcNAc residue on the protein. Examples of these include, but are not limited to Endo A, Endo BH, Endo CE, Endo D, Endo F1, Endo H, Endo M, Endo T (see also WO2006/050584), and ENGase. Other examples are known to the skilled person and can for instance be found on www.cazy arg, in particular under the Glycoside Hydrolase Family 85 and 18. Particularly envisaged is the use of the Endo T enzyme from *Hypocrea jecorina* (formerly known as *Trichoderma reesei*) that is described in WO2006/050584 (see e.g. SEQ IDs 9-12 therein).

'Neoglycoforms' can be unexpected N-glycans which may form even in highly engineered strains as a result of an intervention in the N-glycosylation pathway through heterologous expression, gene deletion or other processes. The responsible glycosyltransferases would have to be identified to initiate their knock-out.

In the present invention we show that neoglycoforms can be removed by endoglucosaminidases and their removal leads to glycoproteins which provide a more homogenous glycosylation profile or provide a higher purity while the presence of yeast-specific background is reduced.

Neoglycoforms can for example comprise a $Man_5GlcNAc_2$ N-glycan with a tetra-saccharide modification. The tetra-saccharide ($Glc\alpha1$-$2Man\beta1$-$2Man\beta1$-$3Glc\alpha$-) substitution of the $Man_5GlcNAc_2$ N-glycan can most likely be attached to the innermost $\alpha$-1,3 arm of the mannosyl core. Neoglycoforms can comprise a number of intermediates that re-appear and the intermediates that re-appear can comprise $Man_5GlcNAc_2$. The $Man_5GlcNAc_2$ N-glycan can be substituted with a linear hexosyl-saccharide that contains β-mannose and/or glucose. The neoglycoforms can comprise $Hex_{6-9}GlcNAc_2$ N-glycans and even $Hex_{6-11}GlcNAc_2$ N-glycans. In addition, certain neoglycoforms may contain one or more phosphomannose residues.

In a specific embodiment the invention provides a composition comprising a plurality of glycoforms of a recombinant glycoprotein, wherein the N-glycans present on said glycoforms consist of a mixture of complex N-glycans and an N-glycan structure consisting of a single GlcNAc.

It can be advantageous to obtain one predominant glycoform within the mixture of complex N-glycans. Such predominant glycoforms typically result from production of a glycoprotein in a complex N-glycosylation-engineered fungal organism.

In a specific embodiment the composition comprises a plurality of glycoforms of a recombinant glycoprotein, wherein the N-glycans present on said glycoforms consist of a mixture of complex N-glycans and an N-glycan structure consisting of a single GlcNAc is substantially devoid of high-mannose-type N-glycan structures, devoid of hybrid glycan structures and devoid of N-glycan neoglycoforms. The wording "devoid of high-mannose-type N-glycan structures, devoid of hybrid glycan structures and devoid of N-glycan neoglycoforms" means that the N-glycans present on the recombinant glycoprotein are essentially of the complex type N-glycan. In a specific embodiment the composition comprises a plurality of glycoforms of a recombinant glycoprotein, wherein said glycoprotein is produced in a complex N-glycosylation-engineered fungal organism, wherein the N-glycans present on said glycoforms consist of a mixture of complex N-glycans and an N-glycan structure consisting of a single GlcNAc is substantially devoid of high-mannose-type N-glycan structures, devoid of hybrid glycan structures and devoid of N-glycan neoglycoforms.

In yet another specific embodiment the invention provides a composition comprising a plurality of glycoforms of a recombinant glycoprotein, wherein the N-glycans present on said glycoforms comprise a mixture of complex N-glycans and an N-glycan structure consisting of a single GlcNAc wherein the sum of said complex N-glycans and N-glycans consisting of a single GlcNAc are present at a level of higher than 90% of the total N-glycans present on said glycoprotein. The wording "the sum of said complex N-glycans and N-glycans consisting of a single GlcNAc" is equivalent to "the combined complex N-glycans and N-glycans consisting of a single GlcNAc) and refers to the fact that the process (or method) of the invention cannot exclude the complete removal of all non-complex N-glycans (id est the hybrid N-glycans and the high mannose N-glycans, originating in the complex N-glycosylation engineered fungal organism). In any case the sum of the complex N-glycans and N-glycans consisting of a single GlcNAc with respect to the total amount of N-glycans present on the recombinant glycoprotein is present at a level higher than 90%, higher than 93% and in many instances even higher than 98%.

In yet another specific embodiment the invention provides a composition comprising a plurality of glycoforms of a recombinant glycoprotein, wherein said glycoprotein is produced in a complex N-glycosylation-engineered fungal organism, wherein the N-glycans present on said glycoforms comprise a mixture of complex N-glycans and an N-glycan structure consisting of a single GlcNAc wherein the sum of said complex N-glycans and N-glycans consisting of a single GlcNAc are present at a level of higher than 90%, higher than 93% or even higher than 98% of the total N-glycans present on said glycoprotein.

In yet another specific embodiment the invention provides a pharmaceutical composition comprising a plurality of glycoforms of a recombinant glycoprotein, wherein the N-glycans present on said glycoforms comprise a mixture of complex N-glycans and an N-glycan structure consisting of a single GlcNAc wherein said complex N-glycans and N-glycans consisting of a single GlcNAc are present at a level of higher than 90%, higher than 93% or even higher than 98% in said mixture.

In yet another specific embodiment the invention provides a pharmaceutical composition comprising a plurality of glycoforms of a recombinant glycoprotein, wherein said glycoprotein is produced in a complex N-glycosylation-engineered fungal organism, wherein the N-glycans present on said glycoforms comprise a mixture of complex N-glycans and an N-glycan structure consisting of a single GlcNAc wherein said complex N-glycans and N-glycans consisting of a single GlcNAc are present at a level of higher than 90%, higher than 93% or even higher than 98% in said mixture.

In another specific embodiment where a recombinant glycoprotein, produced in complex N-glycosylation engineered fungal organism, has at least two functional N-glycosylation acceptor sites then also a plurality of glycoforms are produced when this recombinant glycoprotein is purified from the medium and exogenously contacted with a suitable amount of endoglucosaminidase. In this case also glycoforms of this recombinant glycoprotein will occur on the same recombinant glycoprotein consisting of a single GlcNAc and N-glycans consisting of complex N-glycans. Thus, in the case where 2 functional N-glycosylation sites are present on a glycoprotein theoretically a number of differently mixed glycoforms (e.g. mixtures of single GlcNAc N-glycans and complex N-glycans) will occur. It is understood that the sum of complex N-glycans and N-glycans consisting of a single GlcNAc with respect to the total N-glycans present on said recombinant glycoprotein will be higher than 90%.

Accordingly, in yet another embodiment the invention provides a glycoform of a recombinant glycoprotein having at least two N-glycosylation sites, wherein at least one N-glycosylation site present on said glycoprotein consists of a single GlcNAc and at least one N-glycosylation site on said same glycoprotein consists of a complex N-glycan.

In yet another embodiment the invention provides a pharmaceutical composition comprising a glycoform of a recombinant glycoprotein having at least two N-glycosylation sites, wherein at least one N-glycosylation site present on said glycoprotein consists of a single GlcNAc and at least one N-glycosylation site on said same glycoprotein consists of a complex N-glycan.

In yet another embodiment the invention provides a composition comprising a plurality of glycoforms of a recombinant glycoprotein, wherein the N-glycans present on said glycoforms comprise a mixture of complex N-glycans and an N-glycan structure consisting of a single GlcNAc wherein said complex N-glycans and N-glycans consisting of a single GlcNAc are present at a level of higher than 90% in said mixture wherein said composition is obtained by production of said glycoprotein in a complex N-glycosylation-engineered fungal organism comprising cultivating a recombinant complex N-glycosylation engineered fungal organism comprising an expression vector comprising a genetic construct encoding said glycoprotein under conditions where said glycoprotein is expressed and contacting said recombinant glycoprotein after it has been produced with an endoglucosaminidase.

In yet another embodiment the invention provides a pharmaceutical composition comprising a plurality of glycoforms of a recombinant glycoprotein, wherein the N-glycans present on said glycoforms comprise a mixture of complex N-glycans and an N-glycan structure consisting of a single GlcNAc wherein said complex N-glycans and N-glycans consisting of a single GlcNAc are present at a level of higher than 90% in said mixture wherein said composition is obtained by production of said glycoprotein in a complex N-glycosylation-engineered fungal organism comprising cultivating a recombinant complex N-glycosylation engineered fungal organism comprising an expression vector comprising a genetic construct encoding said glycoprotein under conditions where said glycoprotein is expressed, contacting and purifying said recombinant glycoprotein after it has been produced with an endoglucosaminidase and formulating the resulting plurality of glycoforms of the recombinant protein with an appropriate pharmaceutical excipient (or carrier).

Pharmaceutical compositions containing a composition or glycoform of a specific glycoprotein produced according to the invention can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a composition or glycoform of a specific glycoprotein, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of a composition or glycoform of a specific glycoprotein is preferably that amount which produces a result or exerts an influence on the particular condition being treated. The composition or glycoform of a specific glycoprotein of the present invention can be administered with pharmaceutically acceptable carriers well known in the art using any effective conventional dosage form, including immediate, slow and timed release preparations, orally, parenterally, topically, nasally, ophthalmically, intrathecally, intracerebroventricularly, sublingually, rectally, vaginally, and the like.

The complex N-glycosylation engineered fungal cells as herein may produce a plurality of glycoforms of a recombinant glycoprotein. In the case where only one functional N-glycosylation site occurs on a recombinant glycoprotein one predominant glycoform will carry a complex N-glycan while another glycoform will carry a single GlcNAc. In a specific aspect it may be advantageous to separate these two populations of glycans. For example, it can in certain instances be desirable to work with a recombinant glycoprotein which carries only a complex N-glycan. In these cases, glycoforms carrying only a single GlcNAc can easily be separated from glycoforms carrying a complex N-glycan.

According to alternative particular embodiments, said recombinant glycoprotein has one or more N-glycosylation sites presenting both a single GlcNAc and a plurality of complex N-glycans on the same N-glycosylation site of said glycoprotein.

According to particular embodiments, the recombinant glycoprotein has two or more N-glycosylation sites wherein one or more N-glycosylation sites present on said glycoprotein consist of a single GlcNAc and one or more N-glycosylation sites on said same glycoprotein consist of a plurality of complex N-glycans.

According to particular embodiments, said glycoform of said recombinant glycoprotein has at least three glycosylation sites, wherein at least one N-glycosylation site on said glycoprotein consists of a single GlcNAc and at least another N-glycosylation site consists of a plurality of complex N-glycans.

According to particular embodiments, the endoglucosaminidase enzyme exogenously added to the secreted glycoprotein after production in the complex N-glycosylation engineered fungal organism is a mannosyl-glycoprotein endo-beta-N-acetylglucosaminidase, i.e. it has the activity of E.C. 3.2.1.96 in the IUBMB nomenclature, implying that it can remove sugar chains while leaving one GlcNAc residue on the protein. According to alternative embodiments, the endoglucosaminidase has different affinities towards different types of glycosylation structures. Typical examples of the latter are endoglucosaminidases that are able to hydrolyze hybrid type sugars and/or high-mannose sugars, but are not capable of cleaving complex type glycans. According to further particular embodiments, the endoglucosaminidase is a mannosyl-glycoprotein endo-beta-N-acetylglucosaminidase that has different affinities towards different types of glycosylation structures. According to yet further particular embodiments, the endo-beta-N-acetylglucosaminidase is able to cleave hybrid type sugars and/or high-mannose sugars, but not complex type glycans. According to even more particular embodiments, the endoglucosaminidase is EndoH or EndoT. According to most particular embodiments, the endoglucosaminidase is Endo T.

According to particular embodiments, the at least one enzyme needed for engineering complex N-glycosylation engineered fungal (e.g. yeast) organisms is more than one enzyme. More particularly, the at least one enzyme is the number of enzymes needed to form a pathway for complex glycosylation. Most particularly, each of these enzymes needed for complex glycosylation is targeted so that they act sequentially and in the right order (typically, one enzyme will modify the sugar chain to a substrate for the next enzyme). According to a particular embodiment, the at least one enzyme needed for complex glycosylation is at least one N-acetylglucosaminyl transferase (e.g. GnT I, GnT II, GnT III, GnT IV, GnT V, GnT VI), at least one mannosidase (in particular mannosidase II), at least one fucosyltransferase, at least one galactosyltransferase, at least one sialyltransferase, or any combination of these enzymes.

Examples of glyco-engineered yeasts wherein complex glycosylation pathways have been engineered are extensively described in the art (see e.g. Choi et al., 5022 2003; Hamilton et al.; Science 1244; Wildt et al., 119 2005; Hamilton et al., 387 2007; EP1211310; WO02/000879; US2006148039). In addition, a number of other genes may also be transformed in the glyco-engineered yeast cells described herein to ensure optimal production of complex-type glycosylated glycoproteins, such as ER and Golgi specific transporters (e.g. sym- and antiport transporters for UDP-galactose and other precursors), or enzymes involved in the synthesis of activated oligosaccharide precursors such as UDP-galactose and CMP-N-acetylneuraminic acid. Indeed, the contacting with the at least one enzyme needed for complex glycosylation may occur in the presence of specific glycosyl donors (e.g. sugar nucleotide donors) to ensure efficient and correct glycosylation.

The methods as described herein may be further adapted to ensure that the contact between glycoprotein and endoglucosaminidase occurs under optimal circumstances (i.e. to ensure optimal activity of the endoglucosaminidase on the glycoprotein, e.g. depending on the specific pH, temperature, salt and buffer conditions).

'Contacted' or 'contacting' as used herein does refer to physical proximity between the produced recombinant glycoprotein and the endoglucosaminidase. 'Contacting' in the instant invention occurs in vitro.

The methods as described herein may be further adapted to ensure that the contact between glycoprotein and endoglucosaminidase occurs under optimal circumstances (i.e. to ensure optimal activity of the endoglucosaminidase on the glycoprotein or to ensure the retention of the bioactivity of the glycoprotein itself during and after contact with the endoglucosaminidase).

Contacting between the endoglucosaminidase and the glycoprotein may occur exogenously. It is possible that the contact between the endoglucosaminidase and the glycoprotein happens extracellularly after secretion of the glycoprotein. Depending on the cells and endoglucosaminidase that are used however, the optimal growth and production conditions for the cells (e.g. pH, temperature) may differ from the optimal conditions for enzymatic activity. Thus, the medium where the extracellular contact between the glycoprotein and the endoglucosaminidase takes place may be adjusted for optimal bioactivity of the glycoprotein.

The temperature of the medium may be adjusted to retain optimal bioactivity of the glycoprotein. According to a particular embodiment of the invention the temperature of the medium wherein the contact between the endoglucosaminidase and the glycoprotein takes place is adjusted to 4-37° C. It may be advantageous to adjust the temperature of the medium to 4° C. In other embodiments it might be advantageous to keep temperatures above 37° C.

According to another particular embodiment, the endoglucosaminidase activity is retained at a high salt concentration of the medium. Even if the salt concentration of the medium wherein the contact between the endoglucosaminidase and the glycoprotein takes place is high, the endoglucosaminidase may be able to exert its function on the glycoprotein.

In a specific embodiment the invention provides a composition comprising recombinant N-glycosylated IL-22 or a recombinant N-glycosylated IL-22 thereof with at least 97% amino acid identity, wherein said IL-22 comprises the complex N-glycan $Gal_2GlcNAc_2Man_3GlcNAc_2$ which is present at more than 65% percent of the total complex N-glycans present on said recombinant IL-22.

In another embodiment the invention provides a composition comprising recombinant N-glycosylated IL-22 or a recombinant N-glycosylated IL-22 thereof with at least 97% amino acid identity, wherein said IL-22 comprises the complex N-glycan Gal$_2$GlcNAc$_2$Man$_3$GlcNAc$_2$ which is present at more than 85%, at more than 86%, 87%, 88%, 89%, 90%, 91%, 92%, 93%, 94%, 95%, 96%, 97%, 98% or 99% or 100% of the total complex N-glycans present on said recombinant IL-22.

"At least one mutated N-glycosylation acceptor site" refers to a mutation in the N-glycosylation acceptor site. It is well known in the art that potential N-glycosylation acceptor sites are specific to the consensus sequence Asn-Xaa-Ser/Thr. It must be noted that the presence of the consensus tripeptide is not sufficient to conclude that an asparagine residue (Asn) is glycosylated which is due to the fact that the folding of the protein plays an important role in the regulation of N-glycosylation. It has also been shown that the presence of proline between Asn and Ser/Thr will inhibit N-glycosylation. In the glycoprotein IL-22 there are usually (depending on the mammalian species origin) 3 different N-glycosylation acceptor sites.

In yet another embodiment the invention provides a composition comprising recombinant N-glycosylated IL-22 which has one functional N-glycosylation acceptor site or a recombinant N-glycosylated IL-22 thereof with at least 97% amino acid identity, wherein said IL-22 comprises the complex N-glycan Gal$_2$GlcNAc$_2$Man$_3$GlcNAc$_2$ which is present at more than 85% of the total complex N-glycans present on said recombinant IL-22.

In yet another embodiment the invention provides a composition comprising recombinant N-glycosylated human IL-22 which has one functional N-glycosylation acceptor site present on position N21 in the sequence depicted in SEQ ID NO: 1 or a recombinant N-glycosylated human IL-22 thereof with at least 97% amino acid identity, wherein said human IL-22 comprises the complex N-glycan Gal$_2$GlcNAc$_2$Man$_3$GlcNAc$_2$ which is present at more than 85% at more than 86%, 87%, 88%, 89%, 90%, 91%, 92%, 93%, 94%, 95%, 96%, 97%, 98% or 99% or 100% of the total complex N-glycans present on said recombinant human IL-22.

SEQ ID NO: 1 depicts the amino acid sequence of human IL-22 with one functional glycosylation site only (underlined), id est the glycosylation acceptor site N21 (hIL-22 N21 mutant). The other two glycosylation acceptor sites (marked in SEQ ID NO: 1) are mutated into non-functional N-glycosylation acceptor sites.

hIL-22 N21
aminoterminal-
SEQ ID NO: 1
APISSHCRLDKSNFQQPYIT<u>NRT</u>FMLAKEASLADQNTDVRLIGEKLF

HGVSMSERCYLMKQVLQFTLEEVLFPQSDRFQPYMQEVVPFLARLSN

RLSTCHIEGDDLHIQRNVQKLKDTVKKLGESGEIKAIGELDLLFMSL

RNACI-carboxyterminal

SEQ ID NO: 2 depicts the amino acid sequence of human IL-22 with two functional glycosylation sites (underlined), id est the glycosylation acceptor sites N21 and N35 (hIL-22 N21-N35 mutant). The other glycosylation acceptor site (marked in SEQ ID NO: 2) is mutated into a non-functional N-glycosylation acceptor site.

hIL-22 N21-N35
aminoterminal-
SEQ ID NO: 2
APISSHCRLDKSNFQQPYIT<u>NRT</u>FMLAKEASLAD<u>NNT</u>DVRLIGEKLF

HGVSMSERCYLMKQVLQFTLEEVLFPQSDRFQPYMQEVVPFLARLSN

RLSTCHIEGDDLHIQRNVQKLKDTVKKLGESGEIKAIGELDLLFMSL

RNACI-carboxyterminal

SEQ ID NO: 3 depicts the wild type human IL-22 (hIL-22 WT) amino acid sequence with three functional glycosylation sites (underlined)

hIL-22 WT
aminoterminal-
SEQ ID NO: 3
APISSHCRLDKSNFQQPYIT<u>NRT</u>FMLAKEASLAD<u>NNT</u>DVRLIGEKLF HGVSMSERCYLMKQVL<u>NFT</u>LEEVLFPQSDRFQPYMQEVVPFLARLSN

RLSTCHIEGDDLHIQRNVQKLKDTVKKLGESGEIKAIGELDLLFMSL

RNACI-carboxyterminal

In yet another embodiment the invention provides a method for the production of a composition comprising recombinant N-glycosylated IL-22 or a recombinant N-glycosylated IL-22 thereof with at least 97% amino acid identity, wherein said IL-22 comprises the complex N-glycan Gal$_2$GlcNAc$_2$Man$_3$GlcNAc$_2$ which is present at more than 65% percent of the total complex N-glycans present on said recombinant IL-22 as described herein before wherein said composition is produced in a complex N-glycosylation-engineered fungal organism comprising i) cultivating a recombinant complex N-glycosylation engineered fungal organism comprising a genetic construct encoding IL-22 under conditions wherein IL-22 is expressed and contacting said IL-22 after the production with the addition of an endoglucosaminidase enzyme.

In yet another embodiment the invention provides a composition comprising recombinant N-glycosylated IL-22 or a recombinant N-glycosylated IL-22 thereof with at least 97% amino acid identity, wherein said IL-22 comprises the complex N-glycan Gal$_2$GlcNAc$_2$Man$_3$GlcNAc$_2$ which is present at more than 65% percent of the total complex N-glycans present on said recombinant IL-22 wherein said composition is obtained by production of said recombinant IL-22 in a complex N-glycosylation-engineered fungal organism comprising cultivating a recombinant complex N-glycosylation engineered fungal organism comprising an expression vector comprising a genetic construct encoding IL-22 under conditions wherein said IL-22 is expressed and contacting said recombinant IL-22 with the addition of an endoglucosaminidase.

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

Materials and Methods

Materials and Methods Specifically for Example 1: Endoglucosaminidase Clean-Up to Enrich Complex Glycoforms Strains and Media

*Pichia pastoris* GS115 (his4) was used as the wild-type expression host (De Schutter, K. et al., *Nat. Biotechnol.* 27, 561-566 (2009)). To construct the $Gal_2Gn_2M_3$-hIL-$22^{N21}$ and-IL-$22^{WT}$ strains, N-glycan engineering was started from the M5- (Man5) and $GnM_5$-strains ($GnMan_5$) that modify their glycoproteins predominantly with $Man_5GlcNAc_2$ and $GlcNAcMan_5GlcNAc_2$ N-glycans respectively (Vervecken, W. et al., *Appl. Environ. Microbiol.* 70, 2639-2646 (2004)). The clone of the $GnM_5$-strain with the most homogenous hybrid-type $GlcNAcMan_5GlcNAc_2$ N-glycans was transformed with the pGAPKanMnn2DmMan-II after EcoRI-linearization to express glycoproteins modified with the complex-type $GlcNAcMan_3GlcNAc_2$ N-glycans. The pGAPKanMnn2DmMan-II vector encodes a Mannosidase-II from *Drosophila melanogaster* that is targeted to the Golgi through the N-terminal domain of *S. cerevisiae* Mnn2p early-Golgi localized glycosyltransferase. The clone with the most homogenous $GlcNAc_3Man_3$ N-glycans from the $GnM_3$-strain was used for further engineering by transforming the BgII-linearized pGAPHygMnn2rGnT-II, encoding a Golgi-localized β-N-Acetylglucosaminyltransferase-II from *Rattus norvegicus*, to obtain a strain expressing glycoproteins with bi-antennary, complex-type $GlcNAc_2Man_3GlcNAc_2$ N-glycans ($Gn_2M_3$-strain). The clone of the $Gn_2M_3$-strain with the most homogenous $GlcNAc_2Man_3GlcNAc_2$ N-glycans was then transformed with the EcoRV-linearized pGAPNorMnn2SpGal10GalT. This vector encodes a tri-partite fusion of the Mnn2p-Golgi localization domain, the *Schizosaccharomyces pombe* UDP-glucose/-galactose 4-epimerase and human β-1,4 galactosyltransferase-I (GalT-I). The resulting strains modifies its glycoproteins with $Gal_2GlcNAc_2Man_3GlcNAc_2$. The vectors and construct have been described in (Jacobs, P. P. et al., *Nat. Protocols* 4, 58-70 (2008)). The methodology was described extensively in Laukens, B. et al., *Methods Mol. Biol.* 1321, 103-22 (2015).

Strains were kept as glycerol stocks at −80° C. Prior to the experiment, a fresh culture was started up from a glycerol stock by plating on YPD supplemented with BlasticidinS-HCl (100 μg/mL), Zeocin® (100 μg/mL), G418 (500 μg/mL), Hygromycin (100 μg/mL) and Nourseothricin (100 μg/mL). All cultures were grown at 28° C. and stored at 4° C. awaiting further experimentation.

Recombinant Production of EndoT

For recombinant production of EndoT, a wild type strain (NRRL-Y11430) expressing the full size, mature EndoT under control of the AOX1-promoter was constructed. Large scale production was performed in baffled shake flasks on a level of 6 liters (24×250 ml/2 liter flask) (Schoonooghe, S., Leoen, J. & Haustraete, J., *Pichia pastoris. Methods Mol. Biol.* Clifton N J 907, 325-340 (2012)). At the end of induction, the medium was collected by centrifugation at 18,000×g for 30 min at 4° C. and diafiltered to 20 mM Tris pH 7.5. The clear supernatant was applied to a 138 ml Q sepharose FF column XK26×26 (GE Healthcare), equilibrated with 20 mM Tris pH 7.5. The column was eluted with a gradient over 5 column volumes to 1 M NaCl in the same buffer. The elution fractions were analyzed on SDS-PAGE and the EndoT containing fractions were pooled together. Finally, the protein was injected on a Superdex 75 gelfiltration column XK26×52 with PBS as running solution for formulation and to remove minor contaminants. The obtained fractions were analyzed by SDS-PAGE, the concentration was determined using the Micro-BCA assay (Pierce) and the LPS content (Endosafe-PTS) was measured (<1 EU/ml).

The final yield after purification was 0.183 g/L with >95% purity.

Production and Purification of IL-22 Glycoforms

A pre-culture of the hIL-22-expression strains was inoculated in 10 mL YPD supplemented with appropriate antibiotics and grown overnight. The next day, the pre-culture was used to seed 8×250 mL BMGY (pH5.5) in 2 L baffled shake flasks. The cultures were grown and the medium was replenished with BMMY. After the cultures were induced for 48 hours, the supernatant was harvested and subjected to ammonium sulfate precipitation. Briefly, to remove aggregate proteins and remnant cells, the supernatant was saturated by adding ammonium sulfate salt up to 30%. The samples were centrifuged at 16,800 g and the resulting pellet was discarded. The supernatant was further saturated to 80% under continuous stirring. The precipitate containing hIL-22 was harvested by centrifugation. The remaining supernatant was discarded and the pellets were stored at −20° C. until further purification.

For purification, the hIL-22 ammonium sulfate pellets were dissolved in 25 mM MES pH 5.5 and filtered over a 0.22 μm bottletop filter (Millipore) to remove impurities after solubilisation. The filtrate was desalted over a Sephadex G25 XK26/80 column (GE Healthcare) running on 25 mM MES pH 5.5 and previously equilibrated with the same buffer. To remove the bulk of *Pichia* host proteins and to remove potential endotoxins (LPS), the desalted fractions were pooled and loaded on a Q-Sepharose XK16/32 column (GE Healthcare) equilibrated with 25 mM MES pH 5.5 as running buffer. The flowthrough containing hIL-22 was collected and the column was washed extensively prior to eluting with 1 M NaCl in 25 mM MES pH 5.5. The Q-Sepharose flowthrough was then loaded on a Source 15S column equilibrated with the same running buffer. After loading, the column was washed extensively with running buffer and hIL-22 was eluted with a stepwise linear gradient from 0-1 M NaCl in 25 mM MES pH 5.5. The fractions containing predominantly N-glycosylated hIL-22 were polished over a Superdex75 column (GE Healthcare) equilibrated with PBS set to pH 8.0. After polishing, the hIL-22 containing fractions were concentrated using Amicon spin columns (Millipore) with a 10 kDa molecular weight cut-off (MWCO), sterilized over Millex low protein binding 0.22 μm syringe filters (Millipore), and the concentration was determined by BCA (Pierce). The samples were divided in aliquots and stored at −80° C. The purification steps were performed using the Akta Explorer or Akta Pure purification platform (GE Healthcare). Chromatograms were analyzed in Unicorn 5.11 and formatted afterwards in CorelDraw 11.

Protein Analytical Techniques

Proteins were analyzed on 15% Tris-Glycine SDS-PAGE gels. Prior to loading, the samples were supplemented with Laemli loading dye (200 mM Tris-HCl, pH 6.8 containing 40% glycerol, 10% SDS, 0.8% bromophenol blue with 30 mM DTT unless explicitely mentioned otherwise) and heat denatured at 98° C. for 10 minutes. As a molecular weight ladder the Precision Plus Protein All Blue Standard (Bio-Rad) was included. For visualization, the gels were Coommassie stained or transferred to nitrocellulose membranes by Semi-Dry Western Blot (1 mA/cm$^2$). Human IL-22 was visualized using a anti-hIL-22 mouse monoclonal antibody (Abcam, ab134035) diluted 1:1000 in PBST-3% milk. Blots were revealed using anti-mouse HRP-coupled IgG (GE Healthcare) diluted 1:5000 in PBST-3% milk with Lightning ECL Enhanced Chemiluminescence Substrate (Perkin Elmer).

Protein deglycosylation using EndoH or PNGaseF (New England Biolabs) was done following the manufacturer's instructions. Briefly, 5-10 µg purified protein was heat denatured (5 minutes, 98° C.) in 1× Glycoprotein denaturation buffer (0.5% SDS, 40 mM DTT). After cooling the samples, samples for PNGaseF digestion were supplemented with 1% NP-40 and 1× buffer G7 and 1000 NEB Units PNGaseF (equivalent of 15.4 IUB mU/µl, produced in-house) were added. Samples for EndoH digestion were supplemented with 1× buffer G5 and 500 Units of EndoH (NEB). All digests were kept at 37° C. for 2-4 hours prior to loading on SDS-PAGE.

Glycosylation Analysis by Capillary Electrophoresis

For N-glycan analysis by capillary electrophoresis, either 50 µl of the ammonium sulfate fraction or 10 µg of the purified hIL-22 was prepared following the plate-method described by Laroy, W., Contreras, R. & Callewaert, N., *Nat. Protoc.* 1, 397-405 (2006).

Samples for an in-solution EndoT-digest were diluted in 25 mM MES pH5,5 prior to adding 100 ng of recombinant purified EndoT. The samples were incubated overnight and dried. Labeling was done as described before. The APTS-derivatized N-glycans were analyzed on an ABI 3130 capillary DNA sequencer as described previously (Laroy, W., Contreras, R. & Callewaert, N., *Nat. Protoc.* 1, 397-405 (2006)). N-glycans of bovine RNase B ($Man_{5-9}GlcNAc_2$, M5-9) and a dextran ladder consisting of α-1,6-linked glucose residues (Glucose Units, G.U) were both included as references. Data was analyzed with the Genemapper software (Applied Biosystems).

For exoglycosidase sequencing, exoglycosidase treatment of labeled glycans was done with *Streptococcus pneumoniae* β-1,4-galactosidase or β-N-Acetylhexosaminidase (Prozyme, 4 mU per digest), *Trichoderma reesei* α-1,2-mannosidase (produced in our laboratory, 0.33 µg per digest) and Jack Bean α-1,2/-3/-6-mannosidase (Sigma, 20 mU per digest). All the reactions were performed overnight at 37° C. in 20 mM sodium acetate (pH 5.0).

EndoT Dose-Finding for N-Glycoform Clean-Up

In order to determine the impact of EndoT treatment, a single ammonium sulfate pellet (equivalent of 250 mL culture) was re-dissolved in 25 mL of 25 mM MES pH 5.5 and filtered over a 0.22 µm SteriTop/SteriCup bottletop filter (Millipore). The total protein concentration of the filtrate was determined by BCA (Pierce). The protein was divided in two series over sterile eppendorf tubes so that each eppendorf tube contained 1 mg of total protein. A dilution series of recombinant EndoT was made by diluting recombinant EndoT in 25 mM MES pH 5.5 and spiked into the IL-22 containing ammonium sulfate fractions. Each series (from 10 µg EndoT/mg total protein to 0.001 µg/mg) was prepared in duplicate and samples were either incubated at 4° C. or 37° C. overnight (~14 hours). The next day, the samples were evaluated for precipitation. To assess the impact of the EndoT treatment, 1 µL of each sample of both series was loaded on SDS-PAGE for transfer by Western Blot. For Coommassie analysis, 5 µl of each reaction was loaded on SDS-PAGE.

For N-glycosylation analysis, 50 µl of each sample was prepared for capillary electrophoresis (DSA-FACE) as described above. Oligo-mannose background in the N-glycan profile was revealed using an adapted Jack Bean α-mannosidase digestion. Therefore, 1 µL of APTS-labeled N-glycan sample was digested with Jack Bean α-1,2/-3/-6-mannosidase (Sigma, 10 mU per digest). Digests were performed for 2 hours at 37° C. in 20 mM sodium acetate (pH 5.0) prior to analysis by capillary electrophoresis. Longer incubation results in degradation of complex-type N-glycans due to low levels of contaminating β-N-Acetylhexosaminidase and galactosidase in the commercial jack bean preparation.

Purification of EndoT-Treated IL-22 Glycoforms

To purify hIL-22, the ammonium sulfate pellets were dissolved in 25 mM MES pH 5.5 to a final volume of 100 mL and filtered over a 0.22 µm bottletop filter. The total protein concentration of the filtrate was determined by BCA. Next, the filtrate was spiked with recombinant EndoT (0.5-1.0 µg/mg total protein). The reaction was kept at 4° C. (overnight) while gently agitating on a shaker-platform. The next day, the reaction was assessed for precipitation. Precipitate was removed over a 0.22 µm SteriTop/SteriCup bottletop filter and the filtrate was purified as described above.

In Vitro Colo-205 Assay for IL-22 Bioactivity

Human Colo-205 colon carcinoma cells were ordered from the American Type Culture Collection (ATCC) and cultured according to the guidelines provided in the datasheet. Briefly, the cell line was cultured as semi-adherent cells in RPMI1640 (Gibco) supplemented with 10% Fetal Bovine Serum (FBS) at 37° C. 5% $CO_2$. For passaging, cells growing in suspension were collected and the adherent cells were trypsinized following standard tissue culture procedures. For the Colo-205 assay, cells were seeded in 96-well U-bottom plates at $3.0 \times 10^5$ cells/mL (100 µl/well). Cells were allowed to adapt for 24 hours prior to stimulating the cells with a dilution series of hIL-22. All stimulations were allowed to proceed overnight. As control, a dilution series of commercially available recombinant hIL-22 (carrier-free) produced *E. coli* (BioLegend) was used. The next day, the plates were centrifuged at 400 g, 10 minutes at 4° C. and the supernatant was collected. The supernatant was assayed for IL-10 using the hIL-10 DuoSet ELISA (R&D systems). The data was analyzed in GraphPad Prism 6. Specific activity was determined based on the dose-response curve that was used to determine the $EC_{50}$.

Materials and Methods Specifically for Example 2: Clean-Up of ProDerp1 Glycoforms Using EndoT To obtain the different ProDerp1 glycoforms, the pPIC9ProDerp1 *Pichia pastoris* expression vector was transformed into the M5- (Man5) OCH1 mutated *Pichia*-strain that modifies its glycoproteins predominantly with $Man_5GlcNAc_2$ N-glycans (Jacobs, P. P. et al., *Nat. Protocols* 4, 58-70 (2008), Vervecken, W. et al., *Appl. Environ. Microbiol.* 70, 2639-2646 (2004)).

Next the following enzymes were consecutively transformed into this strain using their corresponding OCH1 mutated *Pichia*-strain vector: N-acetylglucosaminyltransferase I, Mannosidase II, N-acetylglucosaminyltransferase II and N-acetylglucosaminyltransferase IV. In between each transformation step, the N-glycan profile of ProDerp1 was analyzed using capillary electrophoresis, and the expression of ProDerp1 was analyzed. Finally a $GlcNAc_3Man_3GlcNAc_2$ ProDerp1 expression strain was obtained.

After a large scale expression experiment, GlcNAc3Man3GlcNAc2 ProDerp1 was purified using a combination of hydrophobic interaction chromatography, anion exchange and gel filtration (final buffer: 50 mM Tris-HCl pH 7.4). In a next step an in vitro GalNAc transfer was performed using the following conditions: 150 µM terminal GlcNAc, 10 mM UDP-GalNAc, 50 mM Tris-HCl pH 7.4+10 mM MnCl2, 0.5 µg human beta-1,4-galactosyltransferase Y285L (specific activity>2,000 pmol/min/µg, R&D Systems) (Ramakrishnan, B. & Qasba, P. K., *J. Biol.*

Chem. 277, 20833-20839 (2002)), overnight incubation at 37° C. To remove the high-mannose background present in GlcNAc3Man3GlcNAc2 and GalNAc3GlcNAc3Man3GlcNAc2 ProDerp1 samples, both samples were treated with EndoT (200 ng of EndoT for 10 µg of glycoprotein, overnight incubation at 37° C.).

EXAMPLES

Example 1

Endoglucosaminidase Clean-Up for Complex Glycoforms of hIL-22$^{WT}$ and hIL-22$^{N21}$ Introduction and Strategy

*Pichia pastoris* was engineered to express hIL-22$^{WT}$ (having 3 functional N-glycosylation sites) modified with complex type Gal$_2$GlcNAc$_2$Man$_3$GlcNAc$_2$ N-glycans. A Gal$_2$Gn$_2$M$_3$-strain expressing the IL-22$^{N21}$ N-glycosylation site mutant (having one functional glycosylation site) was engineered as well, all as described in the materials and methods section.

To remove the structurally heterogeneous background of N-glycans, recombinant endo-β-N-Acetylglucosaminidase from *Trichoderma reesei* (EndoT) was applied.

Results 1.1 EndoT Dose Finding to Clean Up Background N-Glycans

To integrate EndoT in the purification process, it was investigated if the recombinant enzyme could be added prior to purification by adding the endoglucosaminidase just after solubilizing the ammonium sulfate pellets. Since the high salt concentration might not be optimal for enzyme activity a dose-finding experiment at 4° C. was performed first to assess how much EndoT would be required in order to resolve all N-glycan background in the Gal$_2$GlcNAc$_2$Man$_3$GlcNAc$_2$-hIL-22$^{WT}$ sample (FIG. 1).

Then the N-glycans are analyzed by capillary electrophoresis and an effect of EndoT on the N-glycan profile similar to samples incubated at higher temperatures (data not shown) was observed. In detail, when incubation takes place at 4° C. more EndoT is required to reach the same effect. For instance, the peak corresponding to Man$_5$GlcNAc$_2$ only starts decreasing from 0.01 µg EndoT/mg and up to 0.1 µg EndoT/mg is required to clear the remaining Man$_3$GlcNAc$_2$ completely. Similarly, the high mannose N-glycans (M9-10) persist up to 0.01 µg EndoT/mg. To remove the charged phospho-mannose containing N-glycans, up to 0.5 µg EndoT/mg is required. However, when 1 µg EndoT/mg is added, the N-glycan profile was devoid of any oligo-mannose, hybrid or phospho-mannose containing N-glycans. The N-glycans that remain are the same as for the samples incubated at higher temperatures, with no differences between peak intensities when comparing the N-glycan species across other conditions.

Figure 2:
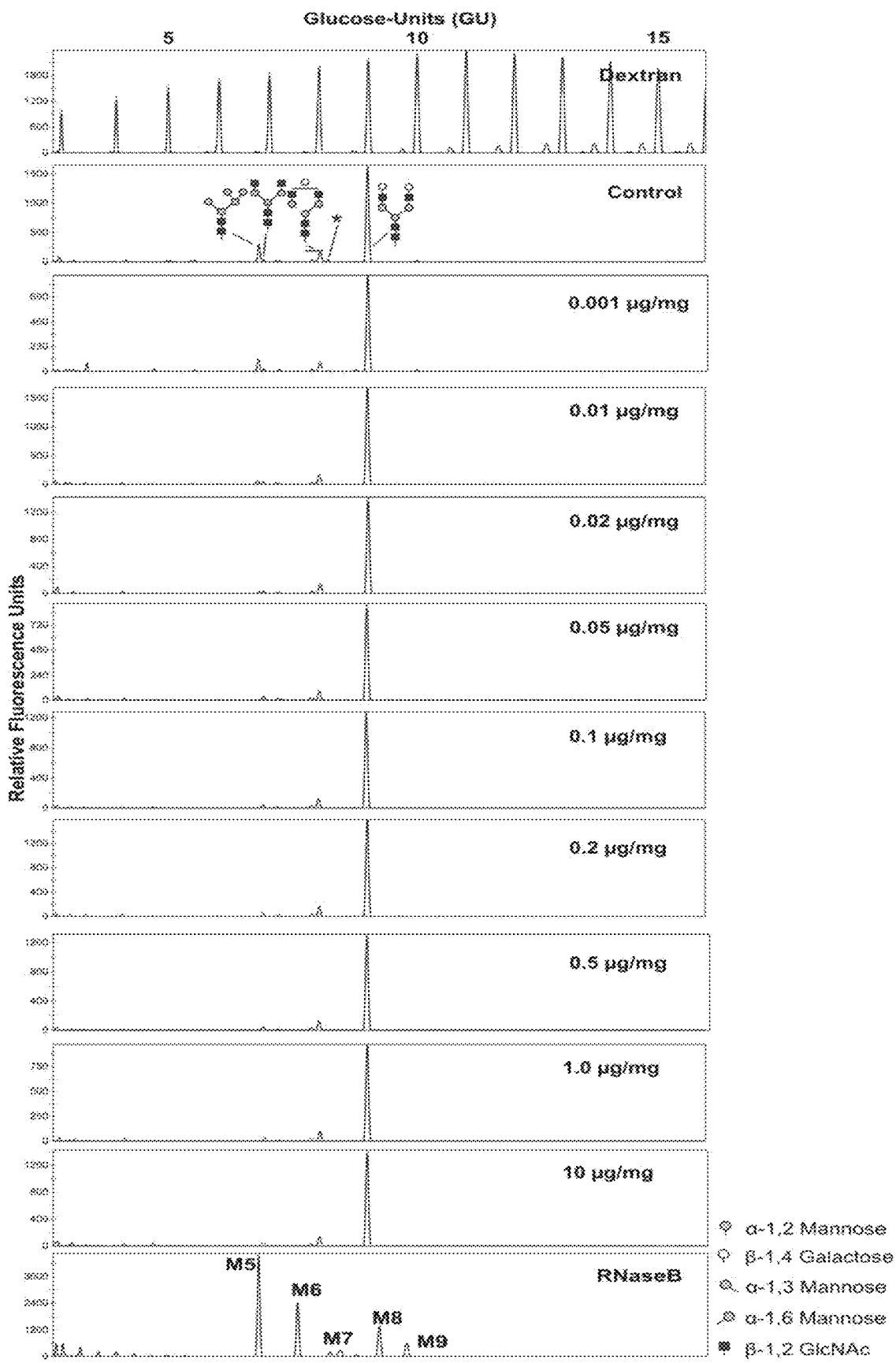
FIG. 2. EndoT dose-finding on the solubilized $Gal_2Gn_2M_3IL-22^{N21}$ ammonium sulfate fraction at 4° C. The ammonium sulfate precipitated fraction was solubilized and equal amounts of total protein were digested overnight at 4° C. with increasing amounts of recombinant EndoT (μg EndoT/mg total protein). Controls were supplemented with an equal volume 25 mM MES pH5.5 but no EndoT. Proposed N-glycan structures are shown. The top panel (dextran) and bottom panel are a dextran reference standard and the $Man_5GlcNAc_2$ (M5-9) reference N-glycans from RNAseB. Symbols in the legend do not take in account the monosaccharides of the core $Man_1GlcNAc_2$ N-glycan. * marks an unidentified N-glycan.

Capillary electrophoresis of the IL-22$^{N21}$ expressing strain (FIG. 2) revealed that the N-glycan profile of the ammonium sulfate fraction that was not treated with EndoT already looks relatively homogenous (see controls in FIG. 2). When the samples were incubated overnight with EndoT, it could be seen that the intensity of the peak corresponding to Man$_5$GlcNAc$_2$ already started to decrease at 1 ng EndoT/mg total protein and that any residual Man$_5$GlcNAc$_2$ completely disappeared from the N-glycan profile at 0.05 µg EndoT/mg. After digestion, any of the minor background peaks that correspond to high-mannose and phospho-mannosyl N-glycans disappeared from 0.01 µg/mg EndoT. At this concentration, almost a single dominant peak corresponding to the Gal$_2$GlcNAc$_2$Man$_3$GlcNAc$_2$ N-glycan was obtained. In addition, a minor fraction consisting of the undergalactosylated GalGlcNAc$_2$Man$_3$GlcNAc$_2$ isomer and nearly no GlcNAc$_2$Man$_3$GlcNAc$_2$ could be seen.

In conclusion, it was observed that the N-glycan heterogeneity correlates with the number of available N-glycosylation sites and thus, it was also determined whether there would be differences with regard to the amount of EndoT that is required to clean up the IL-22 N-glycan profiles. From the above results, it can be concluded that a decrease in N-glycan heterogeneity (e.g. IL-22$^{N21}$ vs. IL-22$^{WT}$) is compatible with a decrease in the amount of recombinant EndoT required to perform the clean-up, as for the current IL-22$^{N21}$ sample only 0.05 µg EndoT/mg was required compared to 0.1 µg EndoT/mg total protein for IL-22$^{WT}$.

1.2 Jack Bean Mannosidase Digestion Reveals and Confirms Background

Because part of the background consists of elaborate high-mannose N-glycans, the signal corresponding to such N-glycans can be very diffuse, and therefore hard to distinguish using a method such as capillary electrophoresis. To circumvent this, a Jack Bean α-1,2/-3/-6-mannosidase digest on the samples that were previously incubated with EndoT at 4° C. (FIG. 3 and FIG. 4) was included.

Figure 3:
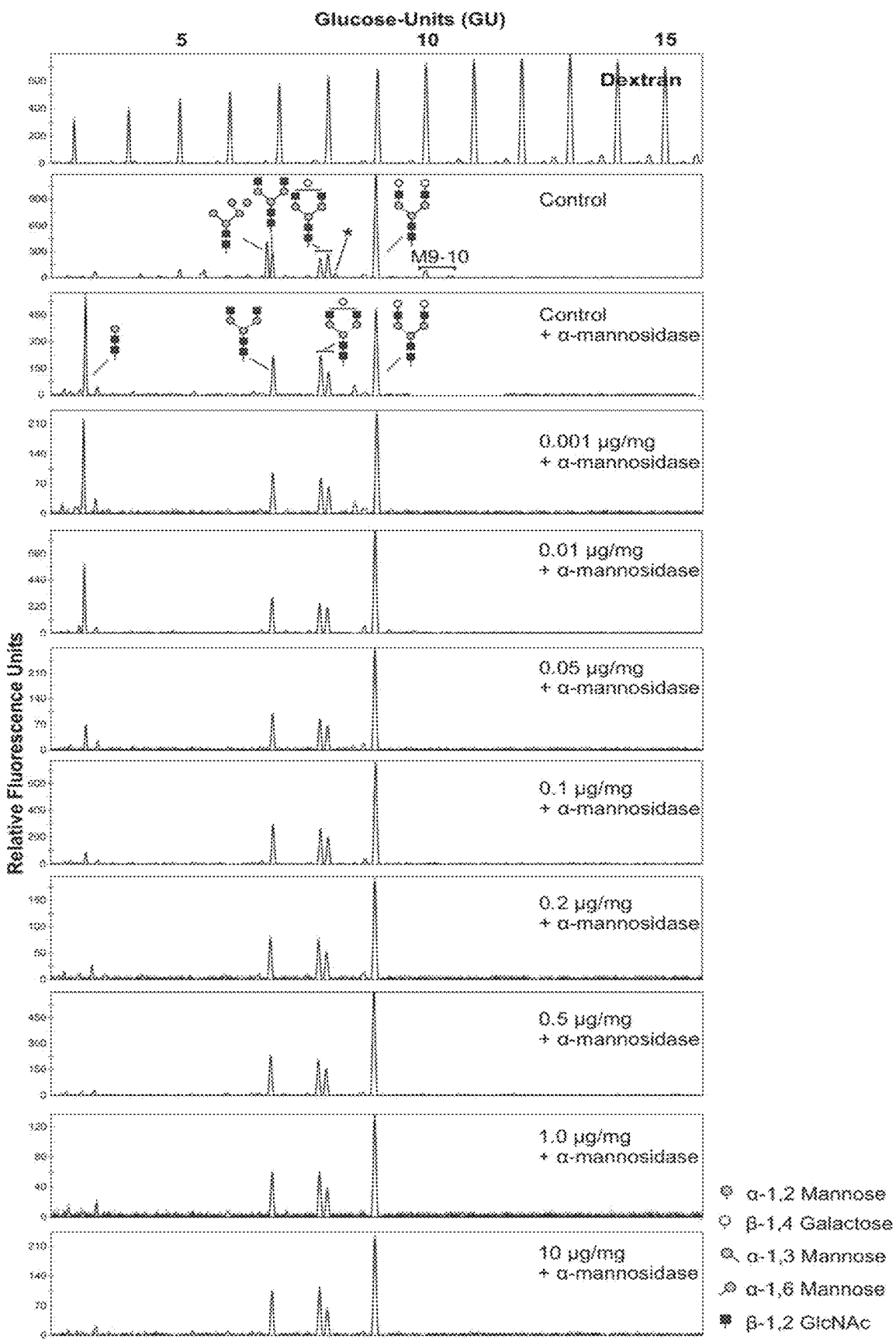
FIG. 3. Jack Bean α-mannosidase digestion reveals residual background. The APTS-labeled N-glycans released from the ammonium sulfate fraction from the $Gal_2Gn_2M_3IL-22^{WT}$ samples that were previously digested with EndoT at 4° C. (indicated in μg EndoT/mg) were incubated briefly with Jack Bean α-mannosidase. The control sample is neither digested with EndoT nor with α-mannosidase and reflects the N-glycan profile of the untreated ammonium sulfate fraction. When the N-glycans of the control sample are digested with α-mannosidase, the core $Man_1GlcNAc_2$ appears as a result of hydrolysis of oligomannose N-glycans. The top panel is a dextran reference ladder (Dextran). Symbols in the legend do not take in account the monosaccharides of the core $Man_1GlcNAc_2$ N-glycan FIG. 4. Jack Bean α-mannosidase digestion reveals minor background. The APTS-labeled N-glycans released from the $Gal_2Gn_2M_3$ IL-$22^{N21}$ samples previously digested at 4° C. with EndoT (indicated in μg/mg) were incubated briefly with Jack Bean α-mannosidase. The control sample is neither digested with EndoT nor with α-mannosidase and reflects the N-glycan profile of the untreated ammonium sulfate fraction. When the N-glycans of the control sample are digested with α-mannosidase, the core $Man_1GlcNAc_2$ appears as a results of hydrolysis of oligo-mannose N-glycans. The top panel is a dextran reference ladder (Dextran). Symbols in the legend do not take in account the monosaccharides of the core $Man_1GlcNAc_2$ N-glycan FIG. 5. SDS-PAGE analysis of EndoT treated hIL-$22^{WT}$. Samples from the EndoT treated ammonium sulfate fractions were analyzed by SDS-PAGE. Panel a. Coomassie stained gel of the dose-finding (shown in μg EndoT/mg total protein) performed at 4° C. The arrow indicates a band that corresponds to recombinant EndoT. Unglycosylated IL-$22^{WT}$ is marked with "0", glycoforms carrying up to three N-glycans are marked with 1 to 3. Smearing due to oligo-mannose background is indicated with an asterisk. Panel b. Western Blot against hIL-22 on the same samples as in the previous panel. Panel c. Overexposure clearly visualizes any remaining background as evidenced by pronounced smearing. The molecular marker (MM) is indicated, molecular masses are in kDa.

To investigate the Gal$_2$Gn$_2$M$_3$IL-22$^{WT}$ samples the control sample (not treated with EndoT or the Jack Bean mannosidase) was compared with the same sample digested with Jack bean mannosidase (FIG. 3). The immediate hydrolysis of the Man$_5$GlcNAc$_2$ N-glycans down to the Man$_1$GlcNAc$_2$ core was seen. However, the peak intensity of the latter peak exceeds the intensity of the Man$_5$GlcNAc$_2$ peak in the undigested sample, indicating that also other N-glycans are hydrolyzed. When the EndoT treated samples were digested, a steady decline in the peak intensity of the Man$_1$GlcNAc$_2$ core N-glycan was observed. The decline of the latter peak is inversely correlated with the amount of EndoT that was used to pre-treat the ammonium sulfate sample. At the point where 0.5 µg EndoT/mg was used, almost no core of Man$_1$GlcNAc$_2$ could be observed anymore after Jack Bean mannosidase digestion.

Figure 4:
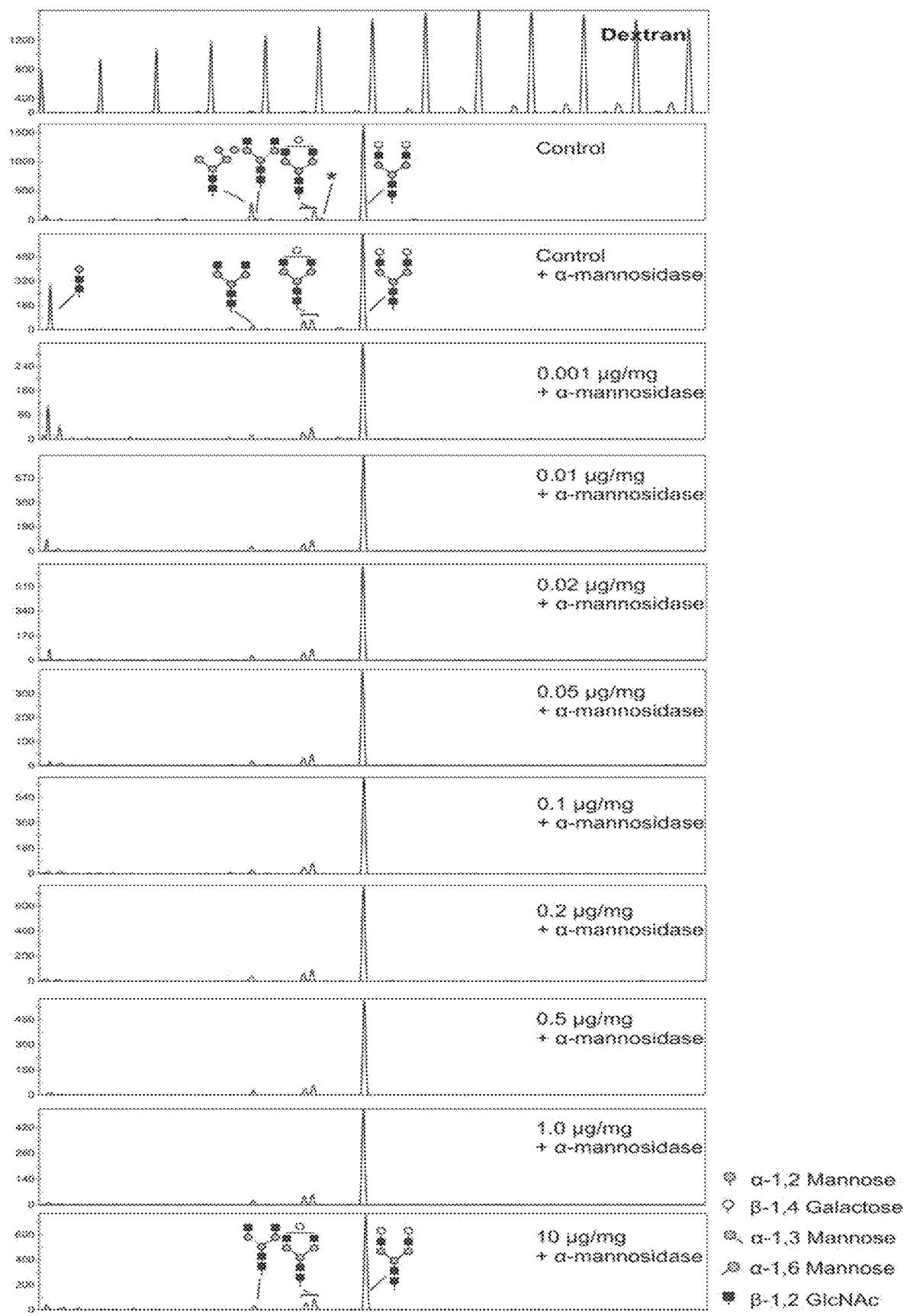

Regarding the N-glycan profile of the Gal$_2$Gn$_2$M$_3$ IL-22$^{N21}$ samples the control samples not treated with EndoT or Jack Bean α-mannosidase already have a relatively homogenous N-glycan profile (FIG. 4). Only some Man$_5$GlcNAc$_2$ in addition to some minor other high-mannose and phosphorylated species was present. When these control samples (not treated with EndoT) are digested with α-mannosidase, a clear peak appeared corresponding to the Man$_1$GlcNAc$_2$ core. The intensity of the latter peak is considerably larger than the amount of Man$_5$GlcNAc$_2$ which was observed in the control samples, indicating that despite the relatively clean N-glycan profile, there is still some background present which could not be detected. However, the Man$_1$GlcNAc$_2$ peak readily declines with increasing concentrations of EndoT up to 0.2 µg/mg EndoT. In conclusion, we could demonstrate that from 0.5 µg/mg and onwards, the core N-glycan did no longer appear and only the dominant Gal$_2$GlcNAc$_2$Man$_3$GlcNAc$_2$ peak, a small amount of the GalGlcNAc$_2$Man$_3$GlcNAc$_2$ undergalactosylated isomer and traces of GlcNAc$_2$Man$_3$GlcNAc$_2$ remain, being all complex N-glycans.

1.3 Monitoring IL22 Stability After EndoT Digestion of IL-22$^{WT}$ and IL-22$^{N21}$ by SDS-PAGE Analysis.

Figure 5:
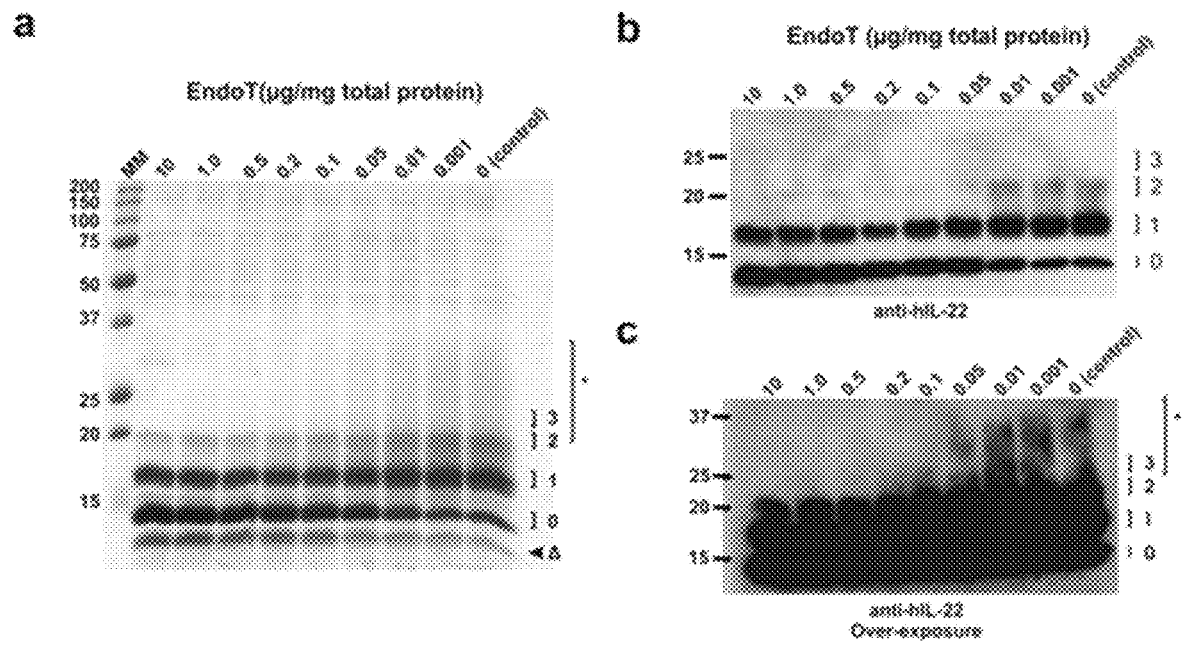
Figure 6:
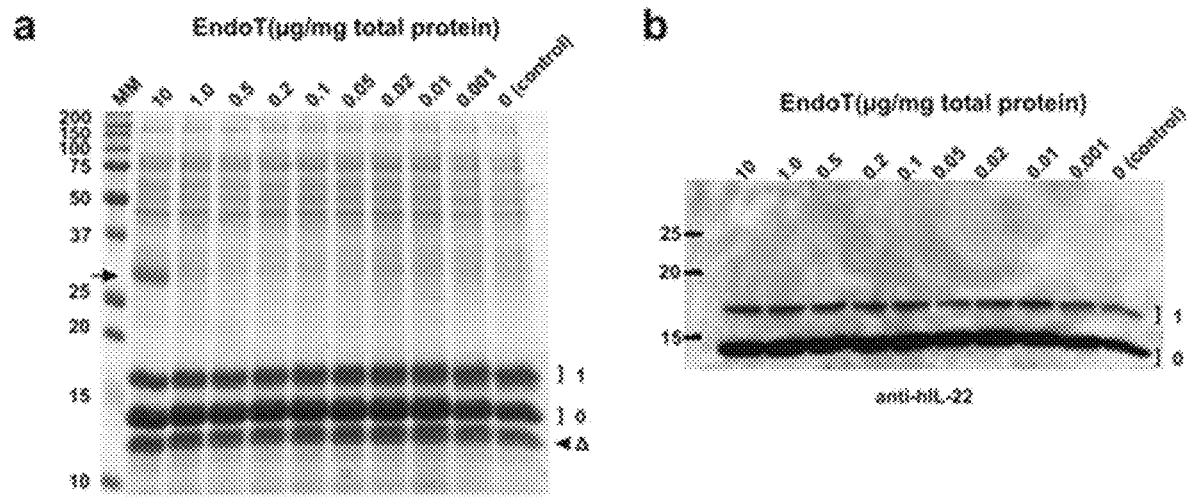
FIG. 6. SDS-PAGE analysis of EndoT treated hIL-$22^{N21}$. Samples from the EndoT treated ammonium sulfate fractions of $Gal_2Gn_2M_3$-IL$22^{N21}$ were analyzed by SDS-PAGE. Panel a. Coomassie stained gel of the dose finding experiment (shown in μg/mg total protein) performed at 4° C. The arrow indicates recombinant EndoT. Unglycosylated IL-22 is marked with "0", the single N-glycoform is marked as "1". Potential degradation is marked with Δ. Panel b. Western Blot against hIL-22 on the same samples as in the previous panel. The molecular weight marker (MM) is indicated in kDa.

The impact of the overnight EndoT-digestion on IL-22 stability was investigated by analyzing the samples on SDS-PAGE (FIG. 5, panel a and FIG. 6, panel a).

It was possible to clearly differentiate between the bands corresponding to unglycosylated IL-22$^{WT}$ and the glycoforms with 1- or-2 N-glycans (FIG. 5, panel a). The fully N-glycosylated glycoform (3 N-glycans) was hard to distinguish on the Coommassie stained gel. In addition, the band that probably corresponds to proteolytic clipping was observed (Δ). The amount of this band increases with rising concentrations of EndoT being added to the sample. A similar pattern was observed for the deglycosylated/non-glycosylated species (0). In the control samples, a diffuse smear between 15- and 37 kDa was noticed that progressively disappears with increasing concentrations of EndoT. At 0.5 μg EndoT/mg total protein, smearing could not be observed any longer.

Analysis by Western Blot using an antibody reactive to IL-22 revealed that the observed diffuse smear was in fact IL-22 and that it indeed disappears with increasing concentration EndoT (FIG. 5, panel b and-c). This could be noticed on both the Coommassie stained gels and on Western Blot; an increase in EndoT causes a decrease in smearing in addition to an increase of unglycosylated IL-22 (both intact and proteolytically clipped), confirming that the smear contains glycoforms of IL-22$^{WT}$.

EndoT treated IL-22$^{N21}$ samples were analyzed as well by SDS-PAGE (FIG. 6, panel a). On the Coommassie stained gel, the bands that correspond to the N-glycosylated IL-22$^{N21}$ could clearly be identified, but no smearing was present in the samples. The samples were analyzed by Western Blot, but also here, no smearing could be seen (FIG. 6, panel b).

The signal of the hyperglycosylated background did not exceed the background signal of the blot (not shown). However, it was seen that the unglycosylated fraction increases with increasing dose of EndoT indicating the removal of some existing background that could not be detected.

1.4 Purification of EndoT-Treated Gal$_2$GlcNac$_2$Man$_3$hIL-22$^{WT}$.

It was investigated whether the EndoT clean-up procedure could be integrated in a purification experiment and it was tested whether the existing protocol also allowed to remove the recombinant EndoT again. In the dose dose-finding experiment, it was established that around 0.5 μg/mg EndoT (per mg of total protein) should be sufficient to clear any oligo-mannose background even when incubating at 4° C. These findings were implemented on the equivalent of a 2 L culture and after determining the total protein concentration of the solubilized ammonium sulfate fractions, EndoT was spiked accordingly. After overnight incubation at 4° C., samples were purified according to a standard protocol (FIG. 7).

After desalting over SephadexG25 (FIG. 7, top left), bulk contaminants were removed over a Q-Sepharose column. The pI of EndoT varies from 4.3-4.4 depending on the processing (Expasy, Compute MW/pI); therefore, EndoT should be retained on the Q-Sepharose column at pH 5.5 (not shown) as are the bulk contaminants from the medium whereas IL-22$^{WT}$ passed in the flowthrough (FIG. 7, top right). Next a S15 Source column was used to separate the different N-glycoforms in the mixture. Any remaining EndoT should be lost in the flowthrough whereas IL-22$^{WT}$ remains bound. Since EndoT also has an acidic pI (~4.2), it should be fairly straightforward to eliminate any residual EndoT during purification using standard chromatographic steps. Moreover, the amount of EndoT that is required is rather limited and should not impact the purification process. Even for a sample such as hIL-22$^{WT}$ with considerable heterogeneity, we obtained highly pure N-glycoforms by adding 0.5-1.0 μg EndoT/mg total protein and incubating at 4° C. Although this needs to be tested on other glycoproteins, a ratio of 1:1000 is suggested as a starting point for further optimization.

Figure 7:
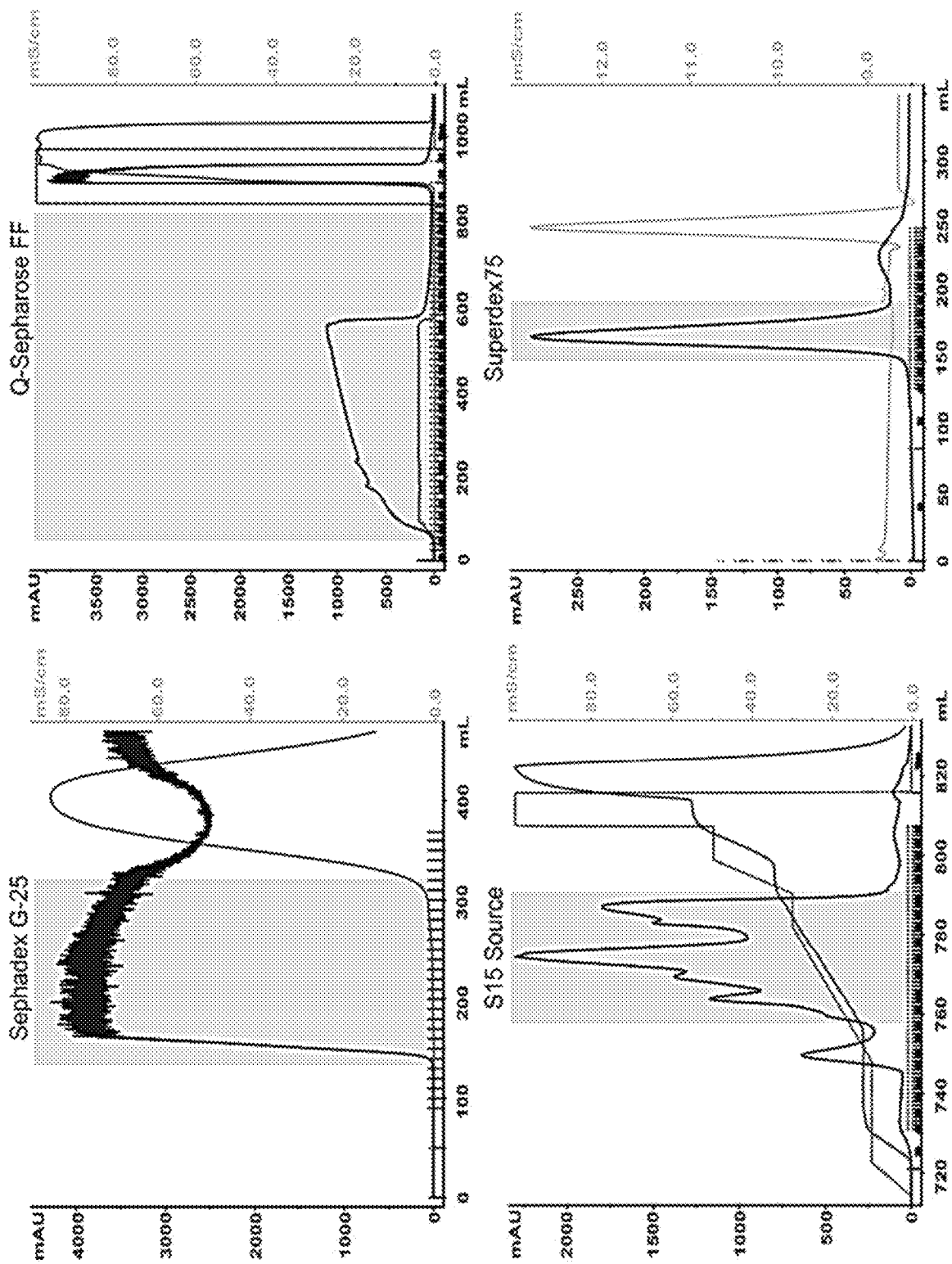
FIG. 7. Purification of EndoT treated hIL-$22^{WT}$. The ammonium sulfate fraction from the $Gal_2Gn_2M_3$-hIL-$22^{WT}$ was spiked with 0.5 μg EndoT/(mg total protein) and kept at 4° C. overnight prior to desalting over a SephadexG25 column (top left). The desalted sample was loaded on Q-Sepharose and the flowthrough was collected, leaving bulk contaminants and the recombinant EndoT on the column (top right). The IL-22 glycoforms were then separated during elution on S15 Source (bottom left). Pure IL-22 glycoforms were pooled and polished over a Superdex75 column (bottom right). Fractions containing IL-22 are indicated in grey. Solid black line: absorbance at 280 nm (mAU), grey line: conductivity (in mS/cm), dotted grey line: the NaCl gradient that was applied to elute the column (0-100% buffer B, not indicated on the axis).
Figure 9:
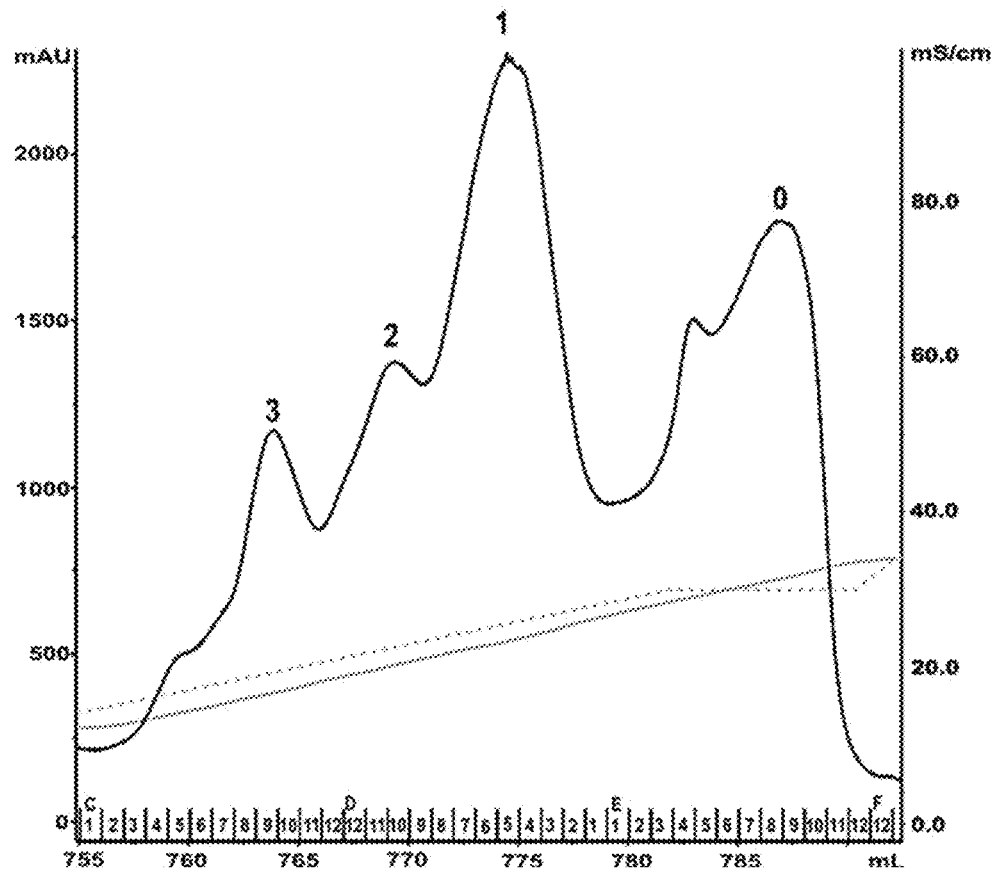
FIG. 9. Glycoform separation during purification of EndoT treated hIL-22. Panel a. A detail of the S15 Source elution profile of the $Gal_2GlcNAc_2$hIL-$22^{WT}$ is shown. The distinct peaks are numbered 1-3 representing glycoforms carrying 1-3 N-glycans respectively. The unglycosylated fractions is indicated with "0". The collected fractions are indicated on the figure. Solid black line line: absorbance at 280 nm (mAU), grey line: conductivity (in mS/cm), dotted grey line: the NaCl-gradient that was applied to eluted the column (not indicated on the axis). Panel b. SDS-PAGE analysis of the S15 Source elution fractions, glycoforms carrying 1-3 or no N-glycans are numbered accordingly. The peak associated with a breakdown product is marked as Δ. Panel c. Based on the elution of the S-Source column, samples were pooled and polished over a Superdex75 column yielding three highly pure fractions (N-glycosylated, a mix fraction and a largely unglycosylated fraction) with differing degree of glycosylation. Panel d. Samples from the N-glycosylated fraction were compared under reducing (+DTT) and non-reducing conditions (−DTT). Panel e. The N-glycosylated pool was differentially digested with PNGaseF(<) that can remove both oligo-mannose and complex N-glycans and with EndoH (*) that only cleave off oligo-mannose or hybrid N-glycans but not complex N-glycans. Glycoforms with differing number of N-glycans are numbered as before (0, 1-3 and Δ for breakdown). Molecular weight marker (MM), masses are given in kDa.
Figure 9:
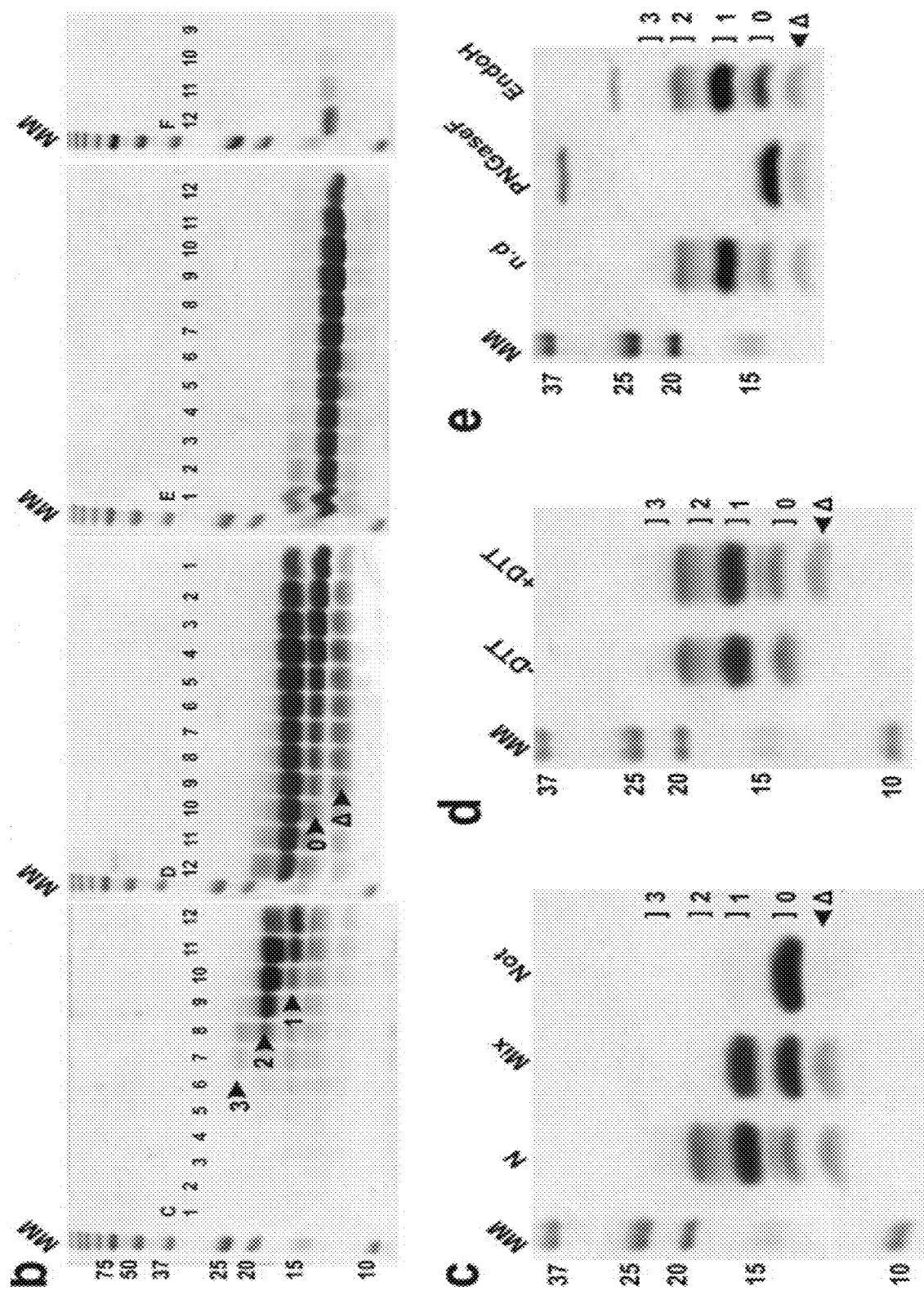

In the elution profile of the Gal$_2$GlcNAc$_2$Man$_3$GlcNAc$_2$-IL-22$^{WT}$ from the S15 Source several peaks can be discriminated (FIG. 7, bottom left and FIG. 9).

When eluting hIL-22$^{WT}$ from the S15 Source column, any heterogeneity can be rapidly detected. In the elution profile of EndoT-treated Gal$_2$GlcNAc$_2$Man$_3$-hIL-22$^{WT}$, rather discrete peaks were observed (FIG. 9, panel a). When we analyzed the elution fractions on SDS-PAGE, we found that the glycoforms ran as distinct bands with virtually no smearing, indicating strong N-glycan homogeneity (FIG. 9, panel b). Moreover, the peaks in the elution profile are in agreement with the elution time of the different glycoforms observed on SDS-PAGE. Then the elution fractions were pooled based on their N-glycan content and were polished on a Superdex75 column (FIG. 7, bottom right). IL-22 eluted as a single peak, with no signs of aggregation or extensive breakdown and was switched to a suitable buffer for storage. The final polished fractions were analyzed on SDS-PAGE, providing an overview of the final pools showing that a largely N-glycosylated fraction could be separated in addition to a mixed- and largely unglycosylated fraction (FIG. 9, panel c). Although more degradation was observed under reducing conditions, no sign of oligomerization was seen under reducing and non-reducing conditions (FIG. 9, panel d). In order to test for any remaining background, a differential digest with PNGaseF and EndoH was performed (FIG. 9, panel e). The N-glycosylated fraction was fully deglycosylated by PNGaseF. In contrast, virtually no effect was seen after EndoH digestion, indicating that the N-glycans are largely recalcitrant to EndoH and therefore must be complex-type N-glycans.

Figure 11:
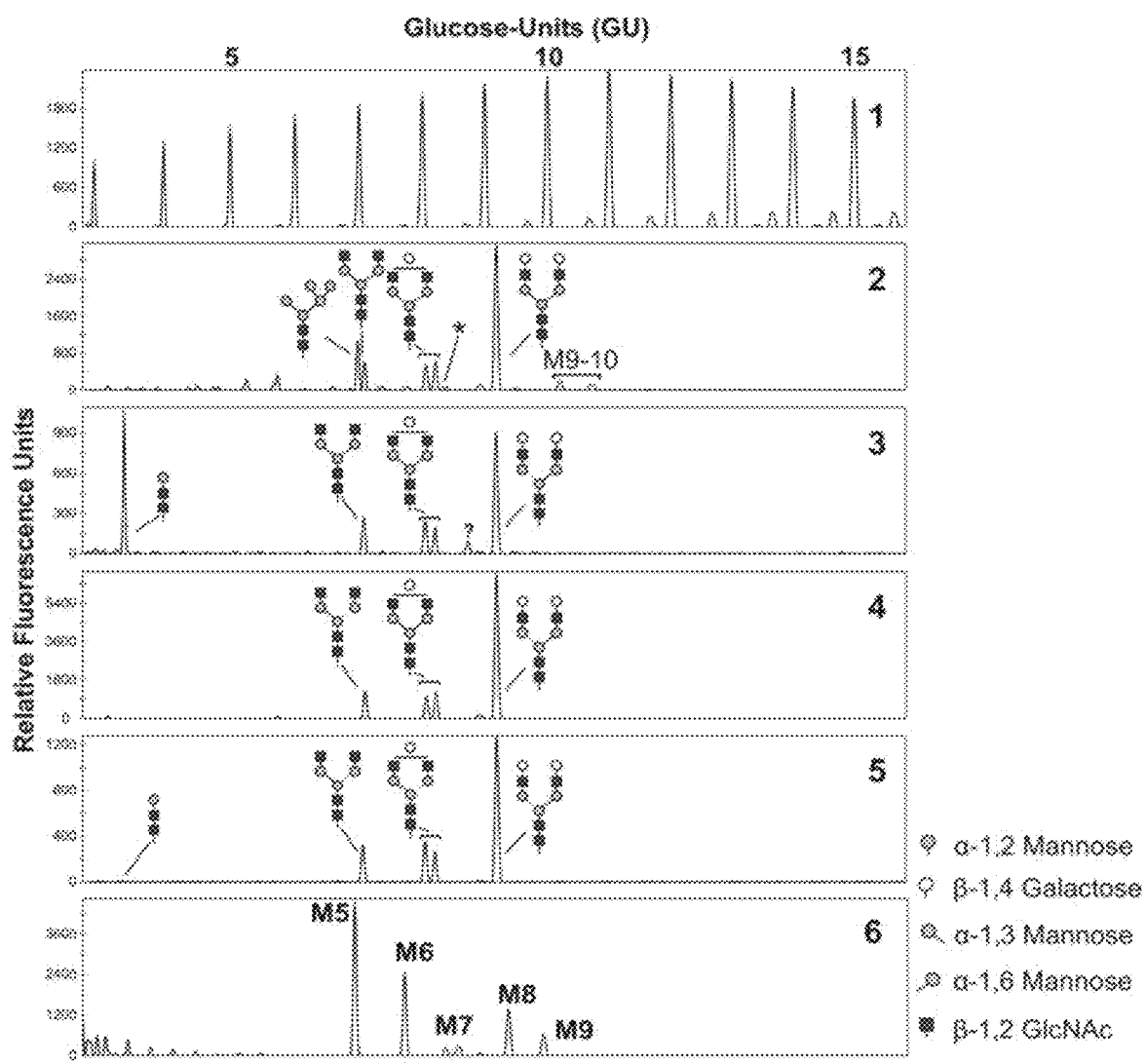
FIG. 11. Control digests on the EndoT treated hIL-$22^{WT}$. Panel a. The APTS-labeled N-glycans from the untreated hIL-22 containing ammonium sulfate fraction (lane 2 & 3) or the EndoT treated purified hIL-22 (lane 4 & 5) were digested with Jack Bean α-mannosidase to reveal the presence of any oligo-mannose background (lane 3 and 5). When the N-glycans of the control sample are digested with α-mannosidase, the core $Man_1GlcNAc_2$ appears as a result of hydrolysis of oligo-mannose N-glycans. Panel b. Exoglycosidase control digest on APTS-labeled N-glycans from purified hIL-22 after EndoT-treatment. Undigested sample shows the dominant peaks in the profile representing $Gal_2GlcNAc_2Man_3GlcNAc_2$ and minor $GalGlcNAc_2Man_3GlcNAc_2$ isomers in addition to residual $GlcNAc_2Man_3GlcNAc_2$ (lane 2). Digestion with a β-1,4-galactosidase removes the galactose residues at the non-reducing end leaving only $GlcNAc_2Man_3GlcNAc_2$ N-glycans (lane 3), further digestion with a β-N-Acetylhexosaminidase removes the terminal GlcNAc moieties leaving only the trimannosyl $Man_3GlcNAc_2$-core (lane 4). Further digestion with Jack Bean α-mannosidase trims the N-glycan down to the core. The control sample is neither digested with EndoT nor with α-mannosidase and reflects the N-glycan profile of the untreated ammonium sulfate fraction. The top panel is a dextran reference ladder (Dextran). The bottom panel represents the reference $Man_{5-9}GlcNAc_2$ N-glycans (M5-9) from RNaseB. * represents an unidentified N-glycan. Another signal we could not explain is marked with "?". Symbols in the legend do not take in account the monosaccharides of the core $Man_1GlcNAc_2$ N-glycan FIG. 12. Control digests on the EndoT treated hIL-22$^{N21}$. Panel a. The APTS-labeled N-glycans from the untreated hIL-22 containing ammonium sulfate fraction (lane 2 & 3) or the EndoT treated purified hIL-22 (lane 4 & 5) were digested with Jack Bean α-mannosidase to reveal the presence of any oligo-mannose background (lane 3 and 5). Panel b. Exoglycosidase control digest on APTS-labeled N-glycans from the EndoT treated purified hIL-22. Undigested sample shows the dominant peaks in the profile supposedly representing $Gal_2GlcNAc_2Man_3GlcNAc_2$ and minor $GalGlcNAc_2Man_3GlcNAc_2$ isomers in addition to residual $GlcNAc_2Man_3GlcNAc_2$ (lane 2). Digestion with a β-1,4-galactosidase removes the galactose residues at the non-reducing end leaving only GlcNAc2Man3GlcNAc2 N-glycans (lane 3), further digestion with a β-N-Acetylhexosaminidase removes the terminal GlcNAc moieties leaving only the trimannosyl Man3GlcNAc2-core (lane 4). Further digestion with Jack bean α-mannosidase trims the N-glycan down to the core. The control sample is neither digested with EndoT nor with α-mannosidase and reflects the N-glycan profile of the untreated ammonium sulfate fraction. When the N-glycans of the control sample are digested with α-mannosidase, the core $Man_1GlcNAc_2$ appears as a result of hydrolysis of oligo-mannose N-glycans. The top panel is a dextran reference ladder (Dextran). Symbols in the legend do not take in account the monosaccharides of the core $Man_1GlcNAc_2$ N-glycan.
Figure 11:
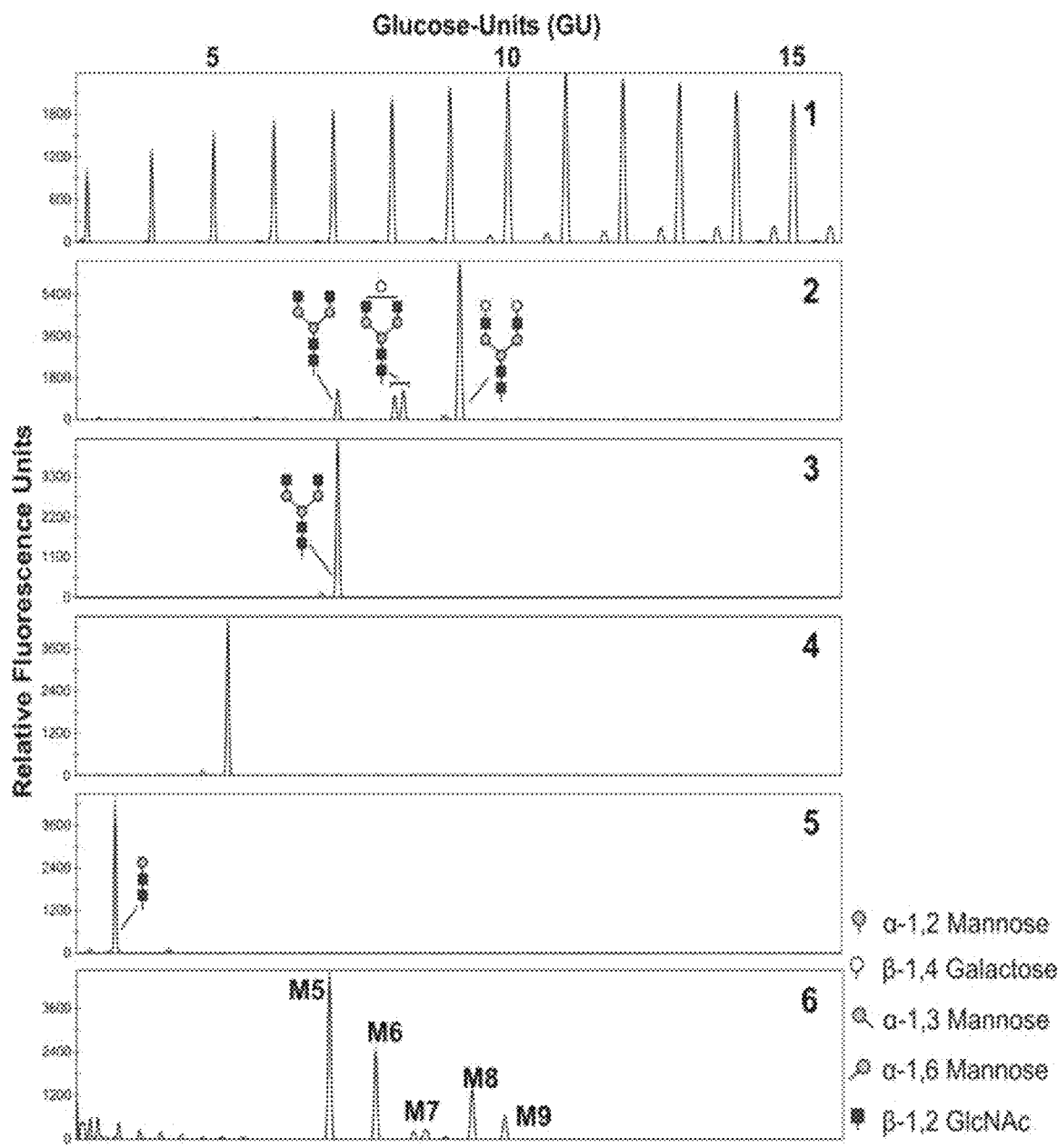

The N-glycosylation profile of the crude, untreated supernatant was compared with that of the newly purified IL-22 that was treated with EndoT (FIG. 11, panel a). In the untreated sample (lane 2), various peaks were seen that correspond to the different pathway intermediates as well as oligo-mannose- and phospho-mannosyl N-glycans. Jack Bean α-mannosidase removes most heterogeneity and reduces it to a single Man$_1$GlcNAc$_2$-peak. The latter peak even exceeds the Gal$_2$GlcNAc$_2$Man$_3$GlcNAc$_2$ peak (lane 3).

In contrast, the EndoT treated sample is more homogenous (lane 4), showing only peaks that correspond to the expected complex N-glycans (Gal$_2$GlcNAc$_2$Man$_3$GlcNAc$_2$, the GalGlcNAc$_2$Man$_3$GlcNAc$_2$ isomer and residual GlcNAc$_2$Man$_3$GlcNAc$_2$). Notably, α-mannosidase digestion does not reveal any background (lane 5) at all, demonstrating the efficiency of this approach.

The identity of the dominant peaks in the spectrum was also confirmed using sequential exoglycosidase digestion (FIG. 11, panel b). Digestion of the N-glycans from the purified, EndoT-treated hIL-22$^{WT}$ (lane 2) with β-1,4-galactosidase cleaves of the galactose residues on the non-reducing end, thereby reducing both the Gal$_2$GlcNAc$_2$Man$_3$GlcNAc$_2$ peak and the undergalactosylated isomers to GlcNAc$_2$Man$_3$GlcNAc$_2$ (lane 3). Digestion with β-N-Acetylhexosaminidase yields the trimannosyl core (lane 4) that is fully reduced to the Man$_1$GlcNAc$_2$ core after Jack Bean α-mannosidase digestion (lane 5).

1.5 Purification of EndoT-Treated Gal$_2$GlcNac$_2$Man$_3$ IL-22$^{N21}$.

Figure 8:
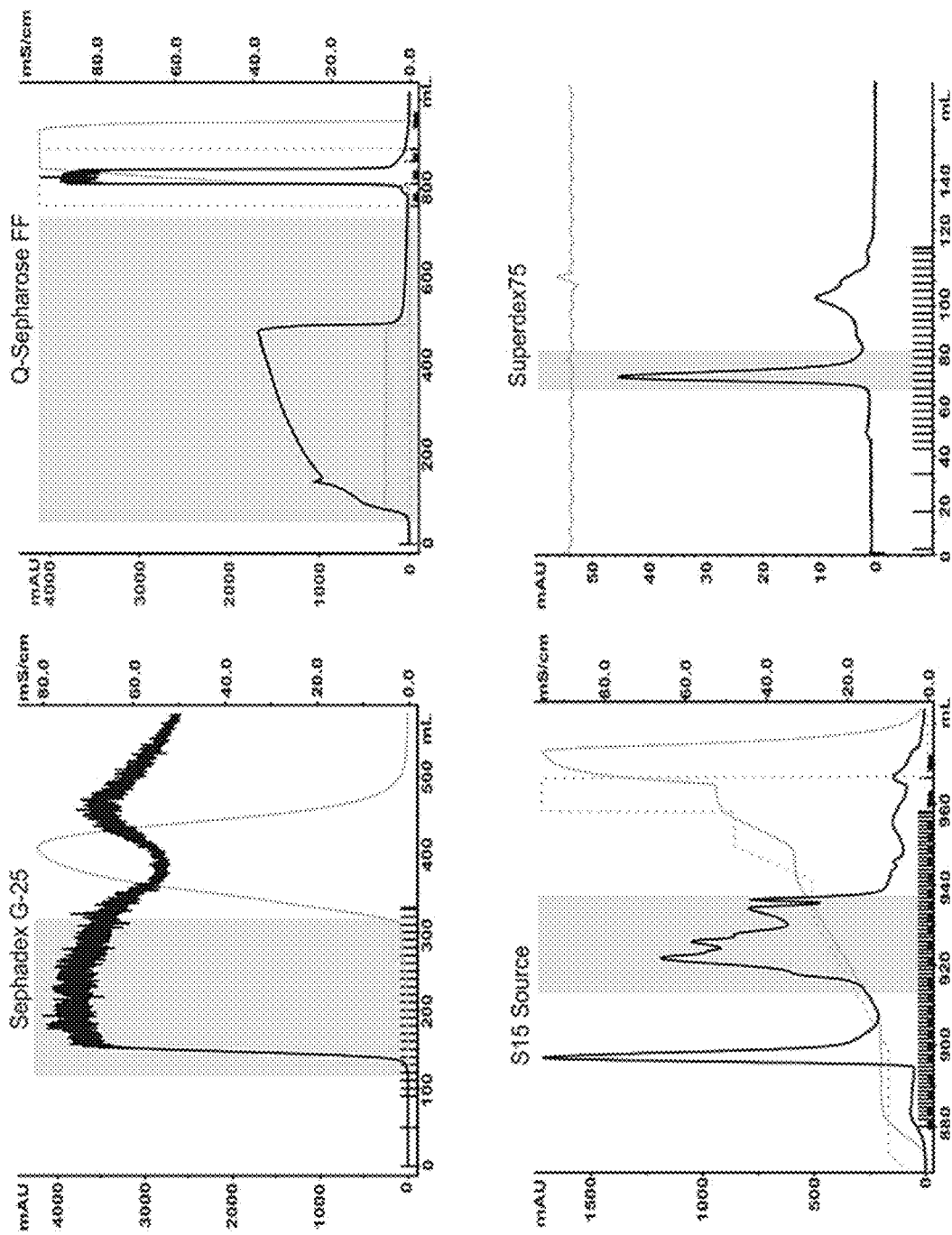
FIG. 8. Purification of EndoT treated hIL-22. The $Gal_2Gn_2M_3$hIL-$22^{N21}$ ammonium sulfate fraction was spiked with 1 μg EndoT/(mg total protein) prior to desalting over a SephadexG25 column (top left). The desalted sample was loaded on Q-Sepharose and the flowthrough was collected. Bulk contaminants including recombinant EndoT are retained on the column until they are eluted with 1 M NaCl (top right). The IL-22 glycoforms were then separated during elution on S15 Source (bottom left). Pure IL-22 glycoforms were pooled and polished over a Superdex75 column (bottom right). Fractions containing IL-22 are indicated in grey. Solid black line: absorbance at 280 nm (mAU), grey line: conductivity (in mS/cm), dotted grey line: the gradient that was applied to eluted the column (0-100% buffer B, not indicated on the axis).

The EndoT clean-up procedure was integrated in the purification scheme. Now this was tested to isolate clean Gal$_2$GlcNac$_2$Man$_3$GlcNAc$_2$ IL-22$^{N21}$. In the dose dose-finding experiment, it was established that from 0.5 µg EndoT/(mg total protein) should be sufficient to clear any oligo-mannose background even when incubating at 4° C. For the preparative digest, the equivalent of 2 L culture was used and after determining the total protein concentration of the solubilized ammonium sulfate fractions, EndoT was spiked in at 1 µg/mg total protein to ensure complete digestion. After overnight incubation at 4° C., samples were purified using the standard protocol (FIG. 8 provides an overview of the purification process).

Figure 10:
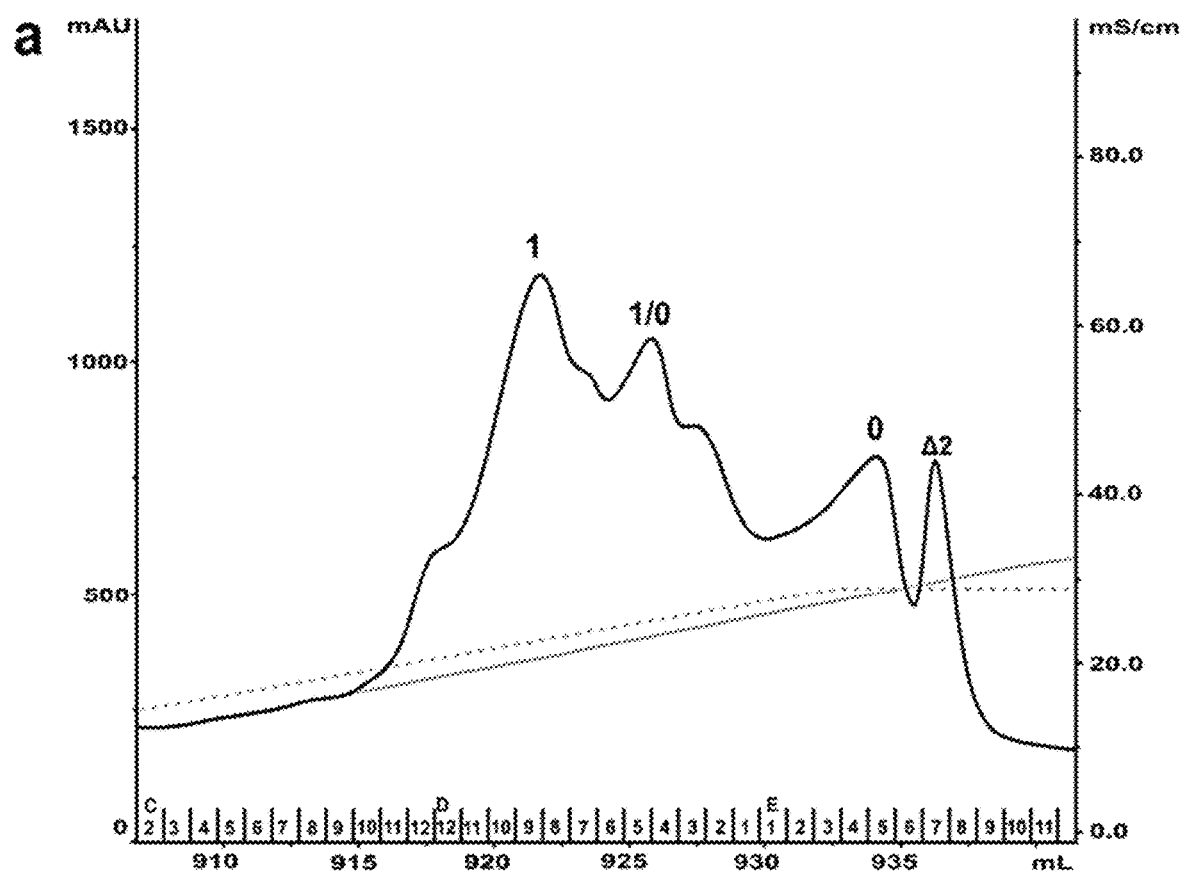
FIG. 10. Glycoform separation during purification of EndoT treated hIL-$22^{N21}$. Panel a. A detail of the S15 Source elution profile of the $Gal_2Gn_2M_3$-hIL-$22^{N21}$ is show. The unglycosylated IL-22N21 is marked with "0". The single glycoform is annotated with "1". The supposed breakdown products are indicated with "Δ". The collected fractions are indicated on the figure. Blue line: absorbance at 280 nm (mAU), brown line: conductivity (in mS/cm), green line: the gradient that was applied to elute the column (not indicated on the axis). Panel b. SDS-PAGE analysis of the S15 Source elution fractions, glycoforms carrying 1 or no N-glycans are numbered accordingly. Breakdown products are marked as "Δ" and "Δ2". Panel c. Based on the elution of the S-Source column, samples were pooled and polished over a Superdex75 column yielding three highly pure fractions with differing degree of glycosylation (N-glycosylated, a mix fraction and a largely unglycosylated fraction). Panel d. Samples from the largely N-glycosylated fraction were compared under reducing (+DTT) and non-reducing conditions (−DTT). Panel e. The N-glycosylated pool was differentially digested with PNGaseF(<) removing both oligo-mannose and complex N-glycans and compared with EndoH (*) that only digests oligo-mannose or hybrid N-glycans but not complex N-glycans. Glycoforms with differing number of N-glycans are numbered as before (0, 1 and Δ for breakdown). Molecular weight marker (MM), masses are given in kDa.
Figure 10:
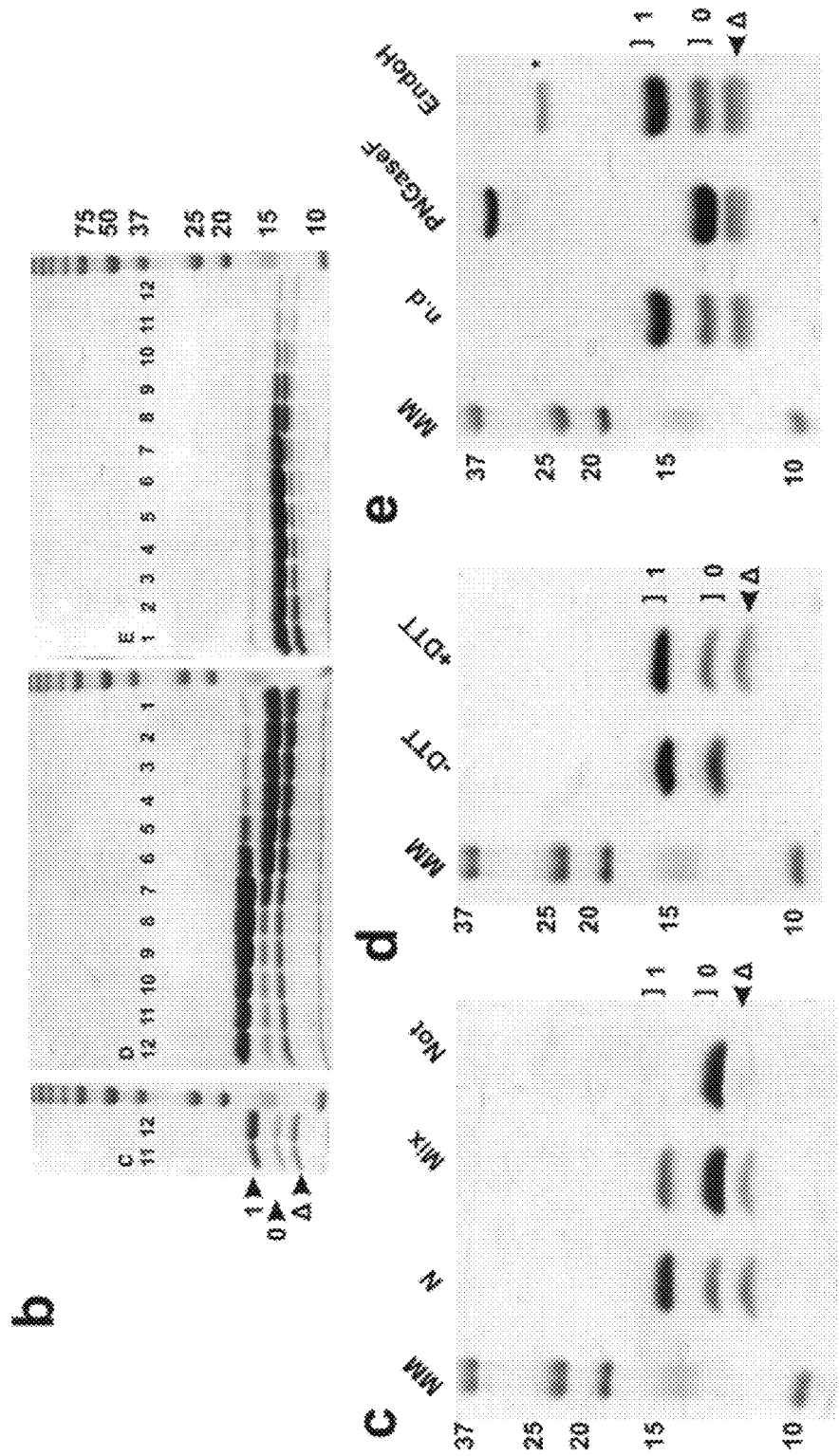

First, the samples were desalted over a SephadexG25 column (FIG. 8 top left) and the eluate was loaded on a Q-Sepharose column. The flowtrough and the wash fractions containing IL-22 were collected whereas bulk contaminants and EndoT were only eluted from the column with 1M NaCl (not shown) (FIG. 8, top right). The IL-22 containing fractions were then loaded on a S15 Source column. The different N-glycoforms of Gal$_2$GlcNAc$_2$Man$_3$GlcNAc$_2$-IL-22$^{N21}$ were eluted between 100 and 300 mM NaCl whereas unglycosylated IL-22$^{N21}$ eluted only at 300 mM NaCl (FIG. 8, bottom left and FIG. 10, panel a). During elution from the S15 Source column, different peaks could be distinguished but they are not completely resolved (FIG. 8, bottom left and FIG. 10, panel a). Analysis of the elution fractions on SDS-PAGE showed a set of clear bands corresponding to unglycosylated IL-22$^{N21}$ and its single glycoform (FIG. 10, panel b). No smearing was observed in the elution fractions, indicating highly homogeneous N-glycoforms. The results from the SDS-PAGE gel are in agreement with the annotation of the peaks in the elution profile. The elution fractions were pooled based on the N-glycan content and were polished over a Superdex75 column (FIG. 8, bottom right). IL-22 eluted as a single peak, with no peaks indicating aggregation or extensive breakdown. The final polished fractions were also analyzed on SDS-PAGE, showing the separation of the largely N-glycosylated fraction in addition to a mixed- and largely unglycosylated fraction (FIG. 10, panel c). Then the N-glycosylated fraction were compared under reducing and non-reducing conditions. No difference except for the presence of a breakdown product when the protein was analyzed under reducing conditions was seen (FIG. 10, panel d). Then it was tested whether there would still be oligo-mannose background by using a differential digest with PNGaseF and EndoH (FIG. 10, panel e). After digestion with PNGaseF, the N-glycosylated fraction was fully deglycosylated but none of the bands was sensitive to digestion with EndoH, indicating the presence of complex N-glycans and only few hybrid or oligo-mannose N-glycans.

Figure 12:
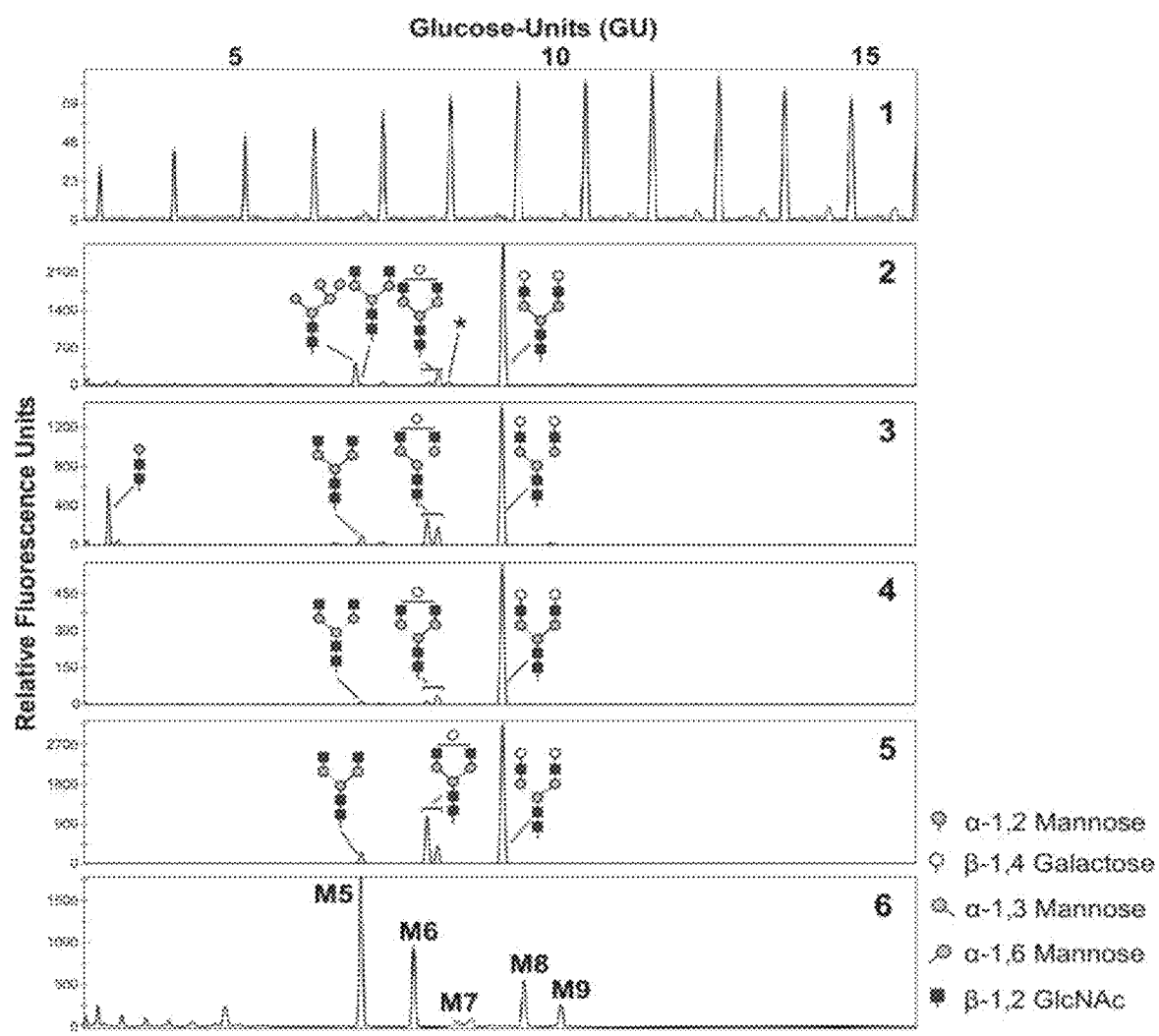
Figure 12:
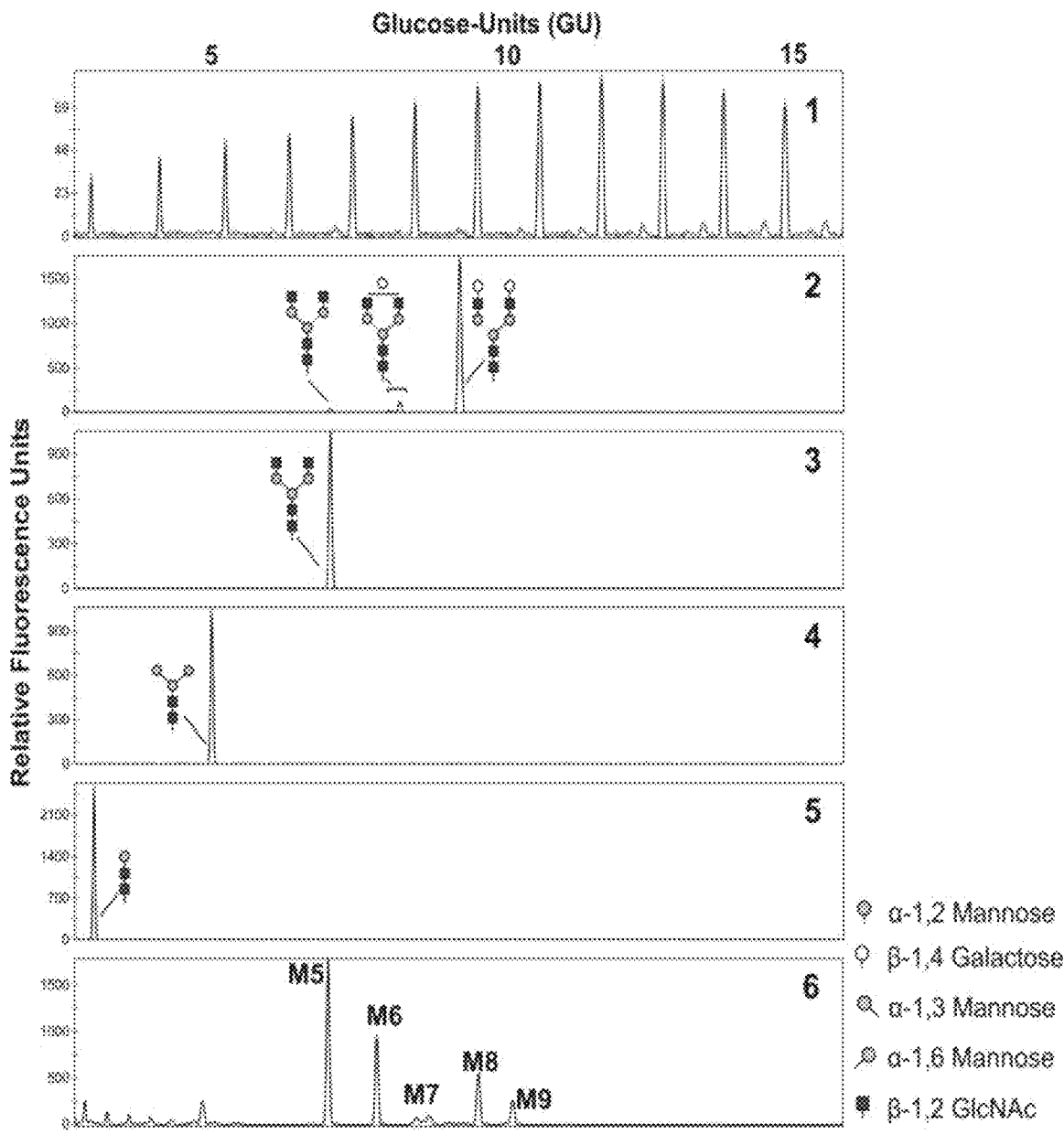

To establish how the EndoT clean-up impacts the N-glycan profile of the purified Gal$_2$GlcNAc$_2$Man$_3$GlcNAc$_2$-hIL22$^{N21}$, the N-glycosylation profile of the untreated ammonium sulfate fraction was compared with that of purified hIL-22$^{N21}$ by capillary electrophoresis (FIG. 12, panel a). In the original sample (lane 2), the peaks that correspond to Gal$_2$GlcNAc$_2$Man$_3$GlcNAc$_2$, the GalGlcNAc$_2$Man$_3$GlcNAc$_2$ isomer and residual GlcNAc$_2$Man$_3$GlcNAc$_2$ were clearly visible, but while also a sizeable portion of Man$_5$GlcNAc$_2$ was seen only traces of oligo-mannose- and phospho-mannosylated N-glycans were present. When a Jack Bean α-mannosidase digest is performed on the untreated sample, the Man$_5$GlcNAc$_2$ is digested down to the Man$_1$GlcNAc$_2$-core. However, the size of the latter peak is more than the amount of Man$_5$GlcNAc$_2$ we observed prior to the digest, indicating that other oligo-mannose N-glycans were present in the sample (lane 3). In contrast, the sample that was treated with EndoT is more homogenous (lane 4), showing only peaks that correspond to the expected complex N-glycans (Gal$_2$GlcNAc$_2$Man$_3$GlcNAc$_2$, the GalGlcNAc$_2$Man$_3$GlcNAc$_2$ isomer and residual GlcNAc$_2$Man$_3$GlcNAc$_2$). It was not possible to reveal any remaining background using α-mannosidase digestion, illustrating the effect of the clean-up step (lane 5). From this results, the trace β-galactosidase activity of the commercial Jack Bean preparation can also be clearly seen by the increase of the undergalactosylated peaks. However, in this experiment, this is not problematic as digestion of the complex type N-glycans has not went further on than to GlcNAc$_2$Man$_3$GlcNAc$_2$. Further digestion would most likely also yield some tri-mannosyl-core and this is absent in the samples.

Then exoglycosidase digestion was used to further confirm the purity of the glycoforms and to confirm the identity of the dominant peaks in the spectrum (FIG. 12, panel b). In the untreated control several smaller peaks outside of the main Gal$_2$GlcNAc$_2$Man$_3$GlcNAc$_2$ peak were seen. However, after β-1,4 galactosidase digestion, only a single GlcNAc$_2$Man$_3$GlcNAc$_2$ peak with no signs of any contaminants remained. Further digestion with HexNAc'ase reduced the latter peak to the Man$_3$GlcNAc$_2$-core. After Jack Bean digestion, the latter peak was then reduced to the Man$_1$GlcNAc$_2$-core. Of note, outside of the complex-type intermediates, no contaminating peaks were seen during exoglycosidase digestion.

1.6 Bio-Activity of EndoT Treated Glycoforms.

Figure 13:
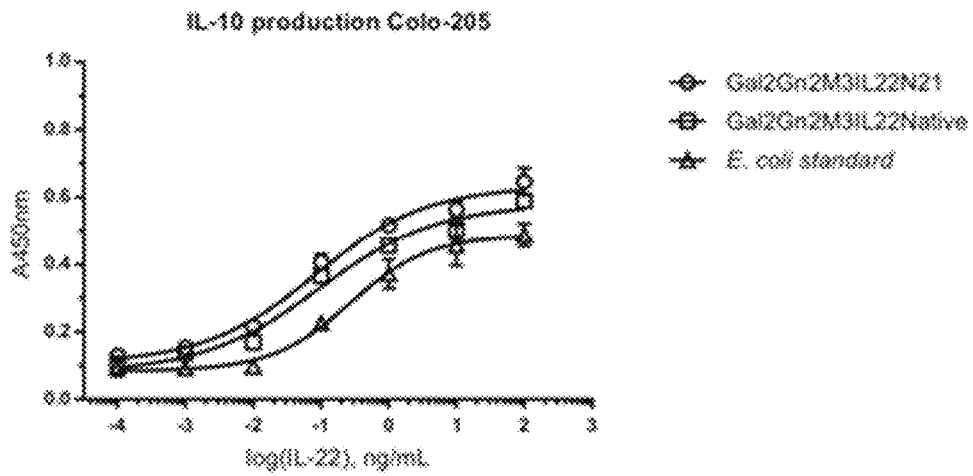
FIG. 13. IL-22-dependent IL-10 secretion in Colo-205 cells. The colon carcinoma Colo-205 cell line was stimulated overnight with a ten-fold serial dilution of purified $Gal_2GlcNAc_2Man_3GlcNAc_2$-hIL22$^{N21}$ or a commercial standard purified from *E. coli*. The next day IL-10 secretion was measured by ELISA. The dose response curve was fitted and the $EC_{50}$ was determined.

In order to determine the bio-activity of the purified Gal$_2$GlcNAc$_2$Man$_3$GlcNAc$_2$-hIL-22$^{WT}$ and-hIL-22$^{N21}$, the glycoforms were tested for their ability to induce IL-10 in the human Colo-205 colon carcinoma cell line. By stimulating with an escalating dose of IL-22 the EC$_{50}$ of the EndoT treated IL-22 was determined and compared with a commercial recombinant IL-22 standard purified from *E. coli* (FIG. 13). The *Pichia*-produced hIL-22 was found to be at least as active as the *E. coli* produced IL-22 (0.094±0.15 ng/mL and 0.082±0.13 ng/mL for hIL-22$^{WT}$ and hIL-22$^{N21}$ respectively versus 0.269±0.14 ng/mL; for *E. coli*-produced IL-22 (EC$_{50}$±SE)).

1.7 Applicability Towards Unexpected Neoglycoforms

Figure 14:
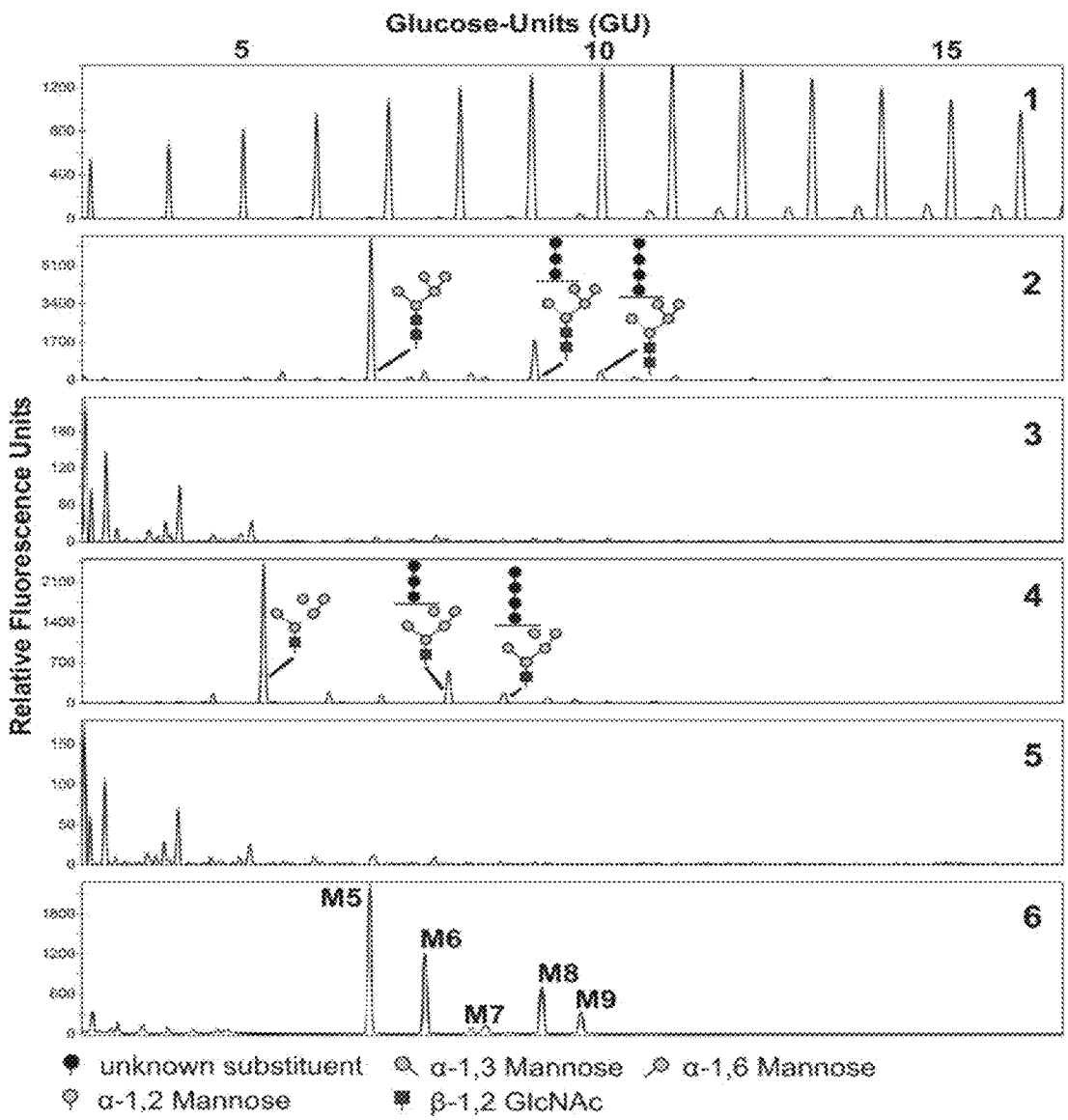
FIG. 14. EndoT cleaves N-glycan neoglycoforms. Lane 2 shows the N-glycans of purified $Man_5GlcNAc_2$ which were prepared using the plate method, showing the expected $Man_5GlcNAc_2$ but also $Man_{8-9}GlcNAc_2$ N-glycans. The latter were identified as novel structures as a result of the N-glycan engineering process. When the same sample is pre-treated with recombinant EndoT, we no longer obtain any signal when the sample is prepared according to the plate-method (lane 3). However, if the EndoT digested sample is labeled directly, the EndoT-released N-glycans can be analyzed (lane 4). The EndoT digested N-glycans have a similar profile as the PNGaseF digested N-glycans but lack the reducing GlcNAc-residue. Lane 5 shows the N-glycan profile of EndoT after direct labeling. Lane 1 shows a dextran reference standard, lane 6 shows the $Man_{5-9}GlcNAc_2$ reference N-glycans from RNaseB (M5-9). The monosaccharide residues of the substitution on hIL-22 have not been fully characterized. Therefore, all monosaccharide constituents are depicted similarly.

During the N-glycan engineering of the various hIL-22-expression strains, an unusual glycoform was encountered that likely results from the recognition of the artificial N-glycan intermediates generated by endogenous glycosyl-transferases. Previously, it was found that the Man$_5$GlcNAc$_2$ N-glycan of a murine IL-22 could be substituted with a linear tetra-saccharide that contains an α1,3-linked glucose, two consecutive β1,2-linked mannose residues and a capping α-1,2-glucose (data not shown). A similar observation was made for human IL-22 expressed in a Man5-strain. However, the N-glycan substitution was one hexose residue smaller. In order to evaluate whether the EndoT clean-up would also work on the neoglycoforms which were identified, an in vitro digest with EndoT on the Man$_5$GlcNAc$_2$hIL-22$^{WT}$ that was purified was tested (FIG. 14). When N-glycans from purified Man$_5$GlcNAc$_2$-hIL-22$^{WT}$ are released with PNGaseF using the plate method (Leroy, W., Contreras, R. & Callewaert, N., *Nat. Protoc.* 1, 397-405 (2006)), the Man$_5$GlcNAc$_2$ N-glycan and the Hex$_{8-9}$GlcNAc$_2$N-glycans that are recalcitrant to α-mannosidase digestion can be identified (lane 2). When the sample is treated with EndoT prior to PNGaseF-release during the preparation of the N-glycans using the plate method, no signal could be detected anymore (lane 3). However, some peaks were seen running early in the electropherograms. These peaks seem to be a contaminating polymer present in the sample (note the equal spacing between these peaks) and not N-glycans.

The same is also seen in lane 5, therefore it could be a contaminating polymer that is present in the purified EndoT that was used in the analysis. The supernatant of the EndoT digest was analyzed using a direct labeling and a similar profile as for PNGaseF released samples was seen but the residues have shift towards the left of the profile with ~1 GU (lane 4). This is consistent with cleavage by an Endo-β-N-Acetylglucosaminidase such as EndoT as it cleaves in between the GlcNAc residues of the chitobiose core. Except for the shift in the glycan profile, the profile was almost identical to the PNGaseF released samples, showing that in addition to $Man_5GlcNAc_2$, that is a known substrate for EndoT, the unusual N-glycan containing the potentially immunogenic β-mannosyl residues is also digested. In addition, no N-glycans on the recombinant EndoT were detected using the plate method (lane 5).

Example 2

Determining the Relative Abundance of Complex N-Glycans on IL-22

N-glycan isolation and analysis was performed on a ABI3130 DNA sequencer as described by Jacobs et al. (Jacobs P P et al. (2009) *Nat. Protoc.* 4(1): 58-70). Peak assignment was done using the ABI GeneMapper software v3.7 (Applied Biosystems). Using the software, the peak intensity and the area under the curve (AUC) of each datapoint was calculated. N-glycan identity was assigned previously using exoglycosidase digestion. To reveal the heterogeneous background (comprising of heterogeneous oligo-mannose N-glycans), each sample was digested with Jack Bean α-mannosidase. After Jack Bean α-mannosidase, the core $Man_1GlcNAc_2$ appears as a consequence of the hydrolysis of the oligo-mannose N-glycans, allowing a more accurate estimate of the background.

The relative quantity of each glycoform within the N-glycan profiles of IL-22$^{N21}$ or IL-22$^{WT}$ glycoform before or after endoglucosaminidase clean-up was determined. To determine the relative abundance, the AUC of peaks that were confirmed by exoglycosidase digestion was calculated over the total AUC of all assigned peaks. The background was defined as the total AUC of the core $Man_1GlcNAc_2$ peak (revealed by Jack Bean α-mannosidase digestion) and peaks that could not be confirmed by exoglycosidase digestion.

Specifically for the $Gal_2GlcNAc_2Man_3GlcNAc_2$ IL-22$^{WT}$ glycoform prior to endoglucosaminidase treatment has 62.15% complex N-glycans (against 37.85% background)—as calculated from the peaks obtained in FIG. 11, panel 3. However, after an Endoglucosaminidase treatment, the complex N-glycan content reaches 93.44% and only 6.56% background remains—as calculated from the peaks obtained in FIG. 11, panel 5. The calculated data are shown in FIG. 19, lower panel.

Specifically for the $Gal_2GlcNAc_2Man_3GlcNAc_2$ IL-22$^{N21}$ glycoform prior to endoglucosaminidase treatment has 80.3% complex N-glycans (against 19.7% background)—as calculated from the peaks obtained in FIG. 12, panel 3. However, after an endoglucosaminidase treatment, the complex N-glycan content reaches 98.3% and only 1.7% background remains—as calculated from the peaks obtained in FIG. 12, panel 5. The calculated data are shown in FIG. 19, upper panel.

Example 3

Determining the Relative Abundance of Galactosylated Glycoforms on IL-22

N-glycan isolation and analysis was performed on a ABI3130 DNA sequencer as described by Jacobs et al. (Jacobs et al. (2009) *Nat. Protoc.* 4(1): 58-70). Peak assignment was done using the ABI GeneMapper software v3.7 (Applied Biosystems). Using the software, the peak intensity and the area under the curve (AUC) of each datapoint was calculated. N-glycan identity was assigned previously using exoglycosidase digestion. Peak calculation on the N-glycosylation profiles of IL-22$^{WT}$ was based on FIG. 11, panel 4 (purified IL-22$^{WT}$ after Endoglucosaminidase clean-up). Peak calculation on the N-glycosylation profiles of IL-22$^{N21}$ was based on the FIG. 12, panel 4 (purified IL-22$^{N21}$ after Endoglucosaminidase clean-up). In the former and the latter N-glycan profiles and the corresponding peak calculation, no Jack Bean digestion is included as the relative abundance of the galactosylated N-glycans is decreased because of reported trace β-galactosidase and hexosaminidase activity in the crude Jack Bean preparation.

The relative quantity of each glycoform within the N-glycan profiles of IL-22$^{N21}$ or IL-22$^{WT}$ glycoform after endoglucosaminidase clean-up was determined. To determine the relative abundance, the AUC of peaks that were confirmed by exoglycosidase digestion was calculated over the total AUC. Peak calculation was based on the FIG. 2, panel 10 (depicted as 1.0 µg/mg).

The relative quantity of bi-antennary $Gal_2GlcNAc_2Man_3GlcNAc_2$ on IL-22$^{N21}$ reaches 88.89% of the total complex N-glycan pool whereas 8.93% carries a single terminal galactose or up to 97% of all complex N-glycans is a bi-antennary complex N-glycan that carries at least a single terminal galactose. The calculated data are shown in FIG. 20, upper panel.

The relative quantity of bi-antennary $Gal_2GlcNAc_2Man_3GlcNAc_2$ on IL-22$^{WT}$ reaches 66.19% of the total complex N-glycan pool. In addition, 22.06% carries a single terminal galactose. Taken together, up to 88.25% is a bi-antennary complex N-glycan that carries at least a single terminal galactose. The calculated data are shown in FIG. 20, lower panel.

Example 4

Clean-Up ProDerp1 Glycoforms Using EndoT

Introduction and Strategy

The aim was to produce different glycoforms of ProDerp1, the enzymatically inactive proform of dominant house dust mite allergen Derp1, containing terminal GalNAc residues.

Results

Figure 15:
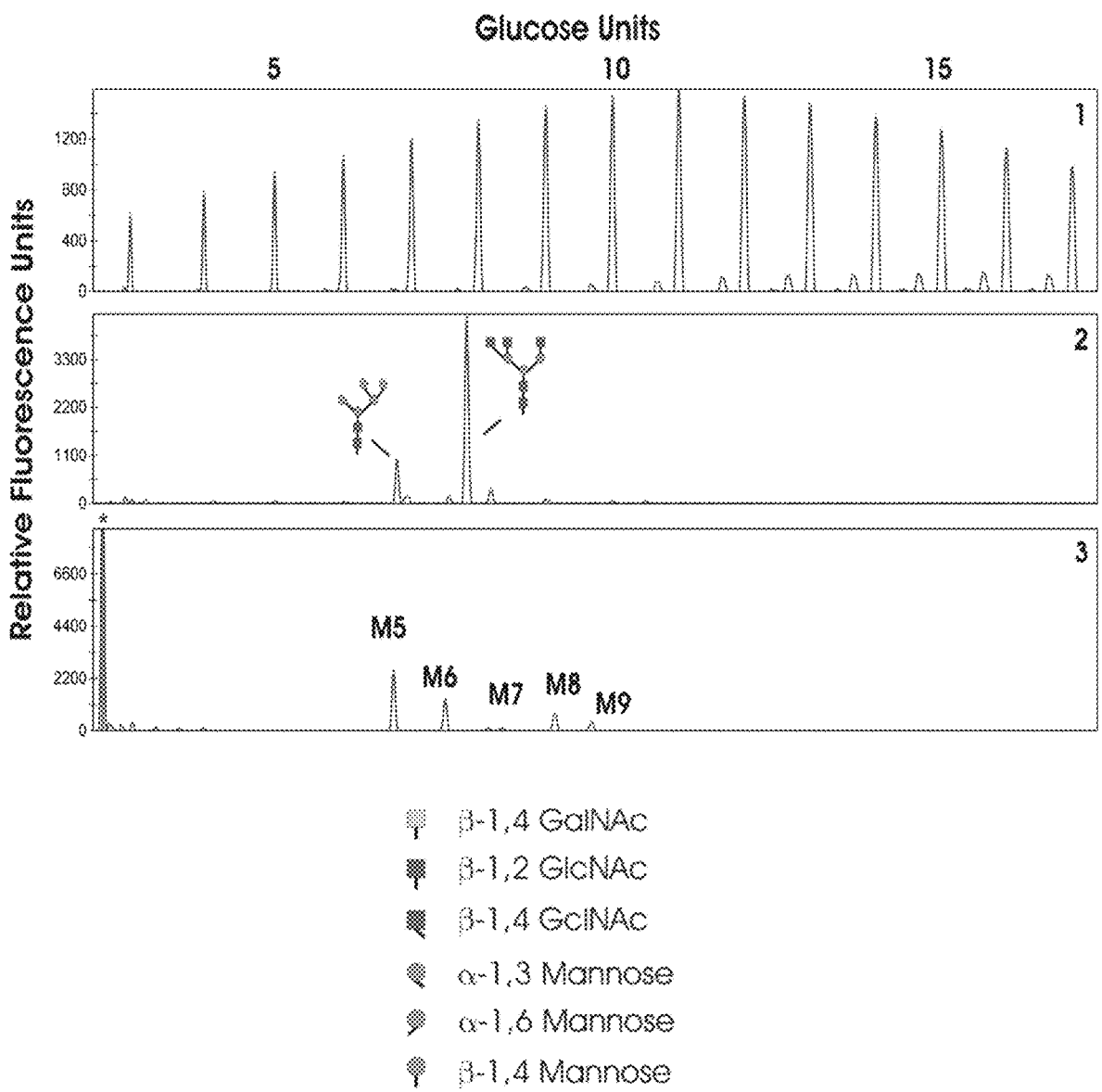
FIG. 15. Capillary electrophoresis profile $GlcNAc_3Man_3GlcNAc_2$ ProDerp1. Panel 1 shows Dextrane standard. Panel 2 shows profile of purified GlcNAc3Man3GlcNAc2 ProDerp1. Panel 3 shows RNaseB standard.
Figure 16:
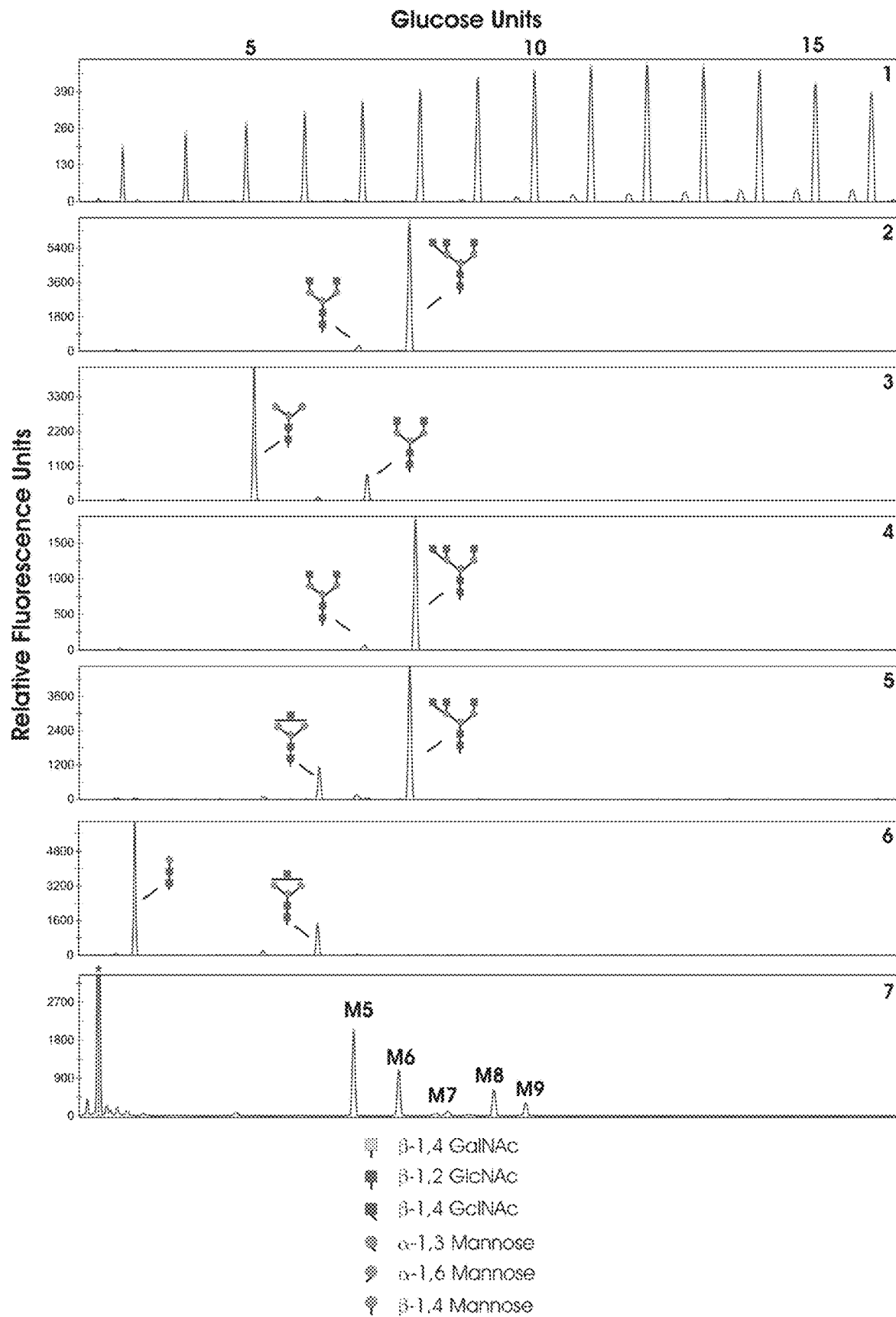
FIG. 16. Capillary electrophoresis profile of $GlcNAc_3Man_3GlcNAc_2$ ProDerp1 treated with EndoT. Panel 1 shows Dextrane standard. Panel 2 shows profile of $GlcNAc_3Man_3GlcNAc_2$ ProDerp1 treated with EndoT to remove high-mannose background. The identity of peaks is confirmed by performing the following exoglycosidase digests: β-N-acetylhexosaminidase (panel 3), α-1,2-mannosidase (panel 4), α-1,2/3/6-mannosidase (panel 5), a combination of β-N-acetylhexosaminidase and α-1,2/3/6-mannosidase (panel 6). Panel 7 shows RNaseB standard.
Figure 17:
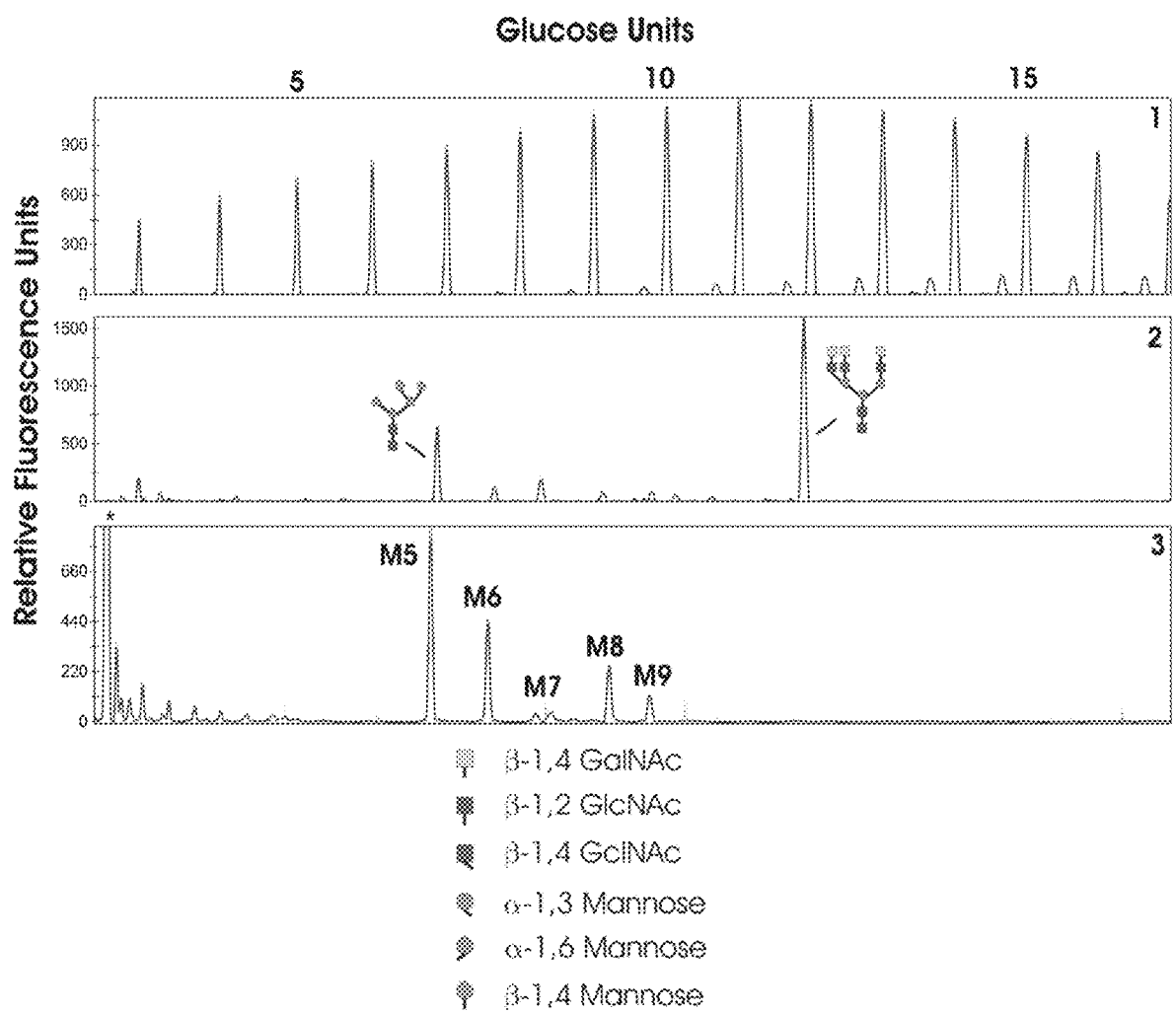
FIG. 17. Capillary electrophoresis profile $GalNAc_3GlcNAc_3Man_3GlcNAc_2$ ProDerp1. Panel 1 shows Dextrane standard. Panel 2 shows profile of $GalNAc_3GlcNAc_3Man_3GlcNAc_2$ ProDerp1. Panel 3 shows RNaseB standard.
Figure 18:
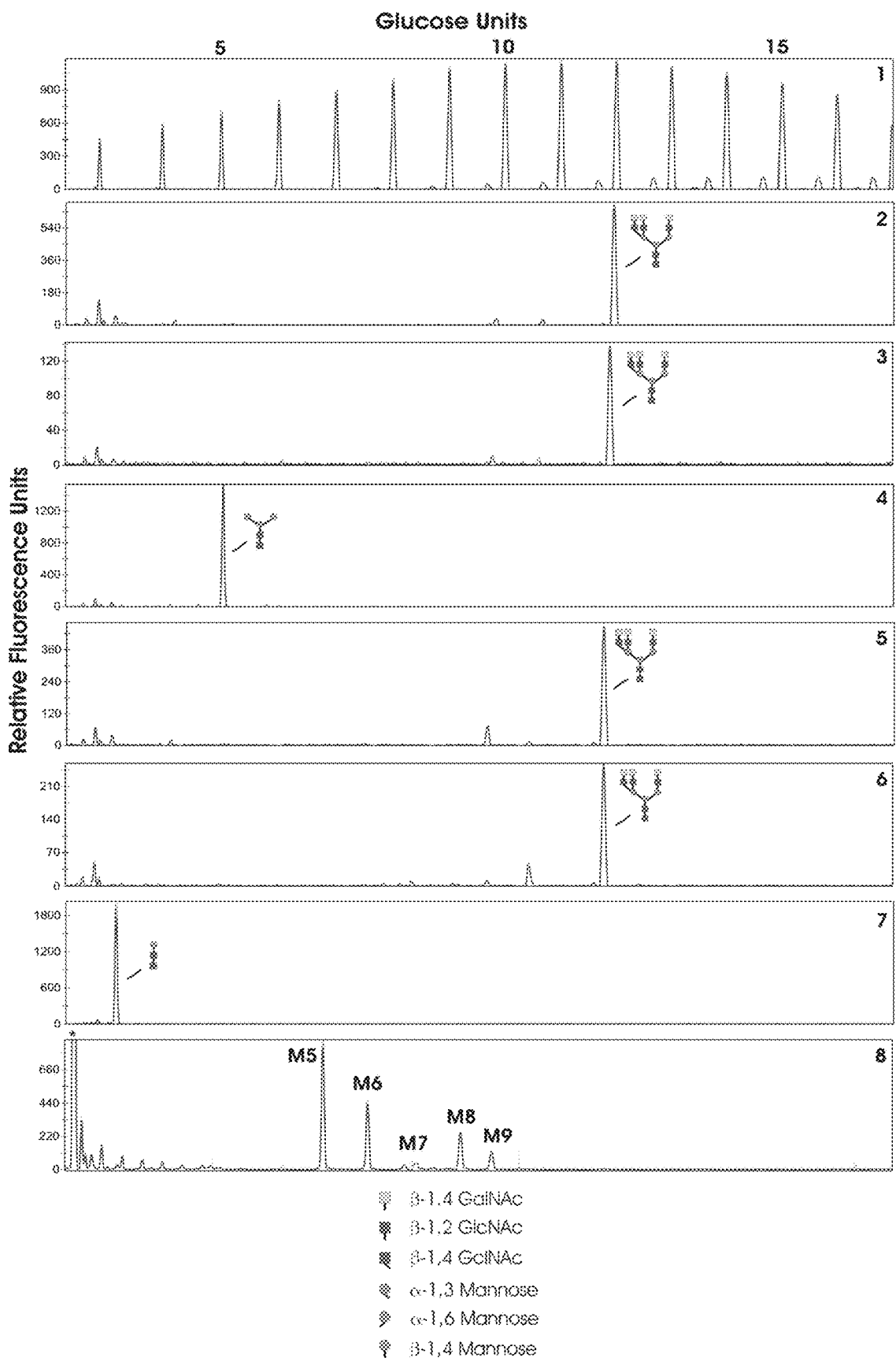
FIG. 18. Capillary electrophoresis profile of $GalNAc_3GlcNAc_3Man_3GlcNAc_2$ ProDerp1 treated with EndoT. Panel 1 shows Dextrane standard. Panel 2 shows the capillary electrophoresis profile of $GalNAc_3GlcNAc_3Man_3GlcNAc_2$ ProDerp1 treated with EndoT to remove high-mannose background. The identity of peaks is confirmed by performing the following exoglycosidase digests: α-1,2-mannosidase (panel 3), β-N-acetylhexosaminidase (panel 4), β-N-acetylglucosaminidase (panel 5), α-1,2/3/6-mannosidase (panel 6), a combination of β-N-acetylhexosaminidase and α-1,2/3/6-mannosidase (panel 7). To detect the difference between GalNAc and GlcNAc we perform a β-N-acetylhexosaminidase digest which is able to remove both terminal GalNAc and GlcNAc residues, whereas a β-N-acetylglucosaminidase is only able to remove terminal GlcNAc residues. Panel 8 shows RNaseB standard.

FIG. 15 shows capillary electrophoresis profile of purified $GlcNAc_3Man_3GlcNAc_2$ ProDerp1. FIG. 16 shows capillary electrophoresis profile of purified $GlcNAc_3Man_3GlcNAc_2$ ProDerp1 treated with EndoT and performed exoglycosidase digests to annotate the different peaks. FIG. 17 shows capillary electrophoresis profile of $GalNAc_3Gn_3Man_3GlcNAc_2$ ProDerp1. FIG. 18 shows capillary electrophoresis profile of $GalNAc_3Gn_3Man_3GlcNAc_2$ ProDerp1 treated with EndoT and performed exoglycosidase digests to annotate the different peaks.

The invention claimed is:

1. A composition comprising:
a recombinant *Pichia pastoris* encoding an exogenous glycoprotein; and
first and second glycoforms of exogenous glycoprotein,
wherein the first glycoform comprises a complex N-glycan;
wherein the second glycoform comprises an N-glycan structure consisting of a single GlcNAc; and
wherein complex N-glycans are more than 90% of the total N-glycans in the composition.

2. A method of producing a composition, the method comprising:
cultivating a complex glycosylation-engineered *Pichia pastoris* encoding an exogenous glycoprotein,
expressing the encoded exogenous glycoprotein,
secreting the expressed exogenous glycoprotein into the medium, and
contacting the secreted exogenous glycoprotein in vitro with a suitable amount of an endoglucosaminidase enzyme
wherein the composition comprises first and second glycoforms of the exogenous glycoprotein,
wherein the first glycoform comprises a complex N-glycan;
wherein the second glycoform comprises an N-glycan structure consisting of a single GlcNAc; and
wherein complex N-glycans are more than 90% of the total N-glycans in the composition.

3. The method according to claim 2, wherein the contacting occurs during purification of the glycoprotein.

4. The method according to claim 2, wherein the contacting occurs after purification of the glycoprotein.

5. The method according to claim 2, wherein contacting with the endoglucosaminidase takes place at a high salt concentration.

6. The method according to claim 3, wherein contacting with the endoglucosaminidase takes place at a high salt concentration.

7. The method according to claim 4, wherein contacting with the endoglucosaminidase takes place at a high salt concentration.

8. The method according to claim 2, wherein the *Pichia pastoris* expresses at least one exogenous nucleic acid sequence encoding an enzyme needed for complex N-glycosylation and/or wherein the *Pichia pastoris* does not express an enzyme involved in the production of high-mannose type structures which enzyme is normally expressed in the wild type *Pichia pastoris*.

9. The method according to claim 2, wherein the endoglucosaminidase enzyme is an endo-beta-N-acetylglucosaminidase of EC3.2.1.96.

10. The composition of claim 1, wherein the composition further comprises a third glycoform;
wherein the third glycofrom comprises a complex N-glycan that is different from the complex N-glycan of the first glycoform.

11. The method according to claim 2, wherein the composition further comprises a third glycoform;
wherein the third glycofrom comprises a complex N-glycan that is different from the complex N-glycan of the first glycoform.

* * * * *

SEQUENCE LISTING

<160> NUMBER OF SEQ ID NOS: 3

<210> SEQ ID NO 1
<211> LENGTH: 146
<212> TYPE: PRT
<213> ORGANISM: Homo sapiens

<400> SEQUENCE: 1

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Gln Asn Thr Asp Val Arg Leu Ile Gly Glu Lys Leu Phe His
        35                  40                  45

Gly Val Ser Met Ser Glu Arg Cys Tyr Leu Met Lys Gln Val Leu Gln
50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile
145

<210> SEQ ID NO 2
<211> LENGTH: 146
<212> TYPE: PRT
<213> ORGANISM: Homo sapiens

<400> SEQUENCE: 2

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Gln
50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile
145

```
<210> SEQ ID NO 3
<211> LENGTH: 146
<212> TYPE: PRT
<213> ORGANISM: Homo sapiens

<400> SEQUENCE: 3

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile
145
```